United States Patent [19]

Hadingham et al.

[11] Patent Number: 5,719,057
[45] Date of Patent: Feb. 17, 1998

[54] STABLY HUMAN TRANSFECTED RODENT FIBROBLAST CELL LINE EXPRESSING HUMAN GABA-A RECEPOTORS, AND CLONED HUMAN GABA-A RECEPTOR SUBUNIT CDNA SEQUENCES

[75] Inventors: Karen Louise Hadingham, Sawbridgeworth; Beatrice le Bourdelles, Harlow; Paul John Whiting, Stansted Mountifichet; Peter Baxter Wingrove, Sawbridgeworth, all of England

[73] Assignee: Merck Sharpe & Dohme Ltd., Hoddeson, England

[21] Appl. No.: 417,330

[22] Filed: Apr. 5, 1995

Related U.S. Application Data

[63] Continuation-in-part of Ser. No. 971,767, Feb. 2, 1993, abandoned.

[30] Foreign Application Priority Data

Jun. 11, 1991 [GB] United Kingdom ............ 9112504
Jun. 9, 1992 [WO] WIPO .............. PCT/GB92/01031

[51] Int. Cl.$^6$ .................................. C12N 5/10
[52] U.S. Cl. .................. 435/357; 435/7.2; 435/69.1; 435/252.3; 435/320.1; 530/350
[58] Field of Search ............... 435/69.1, 7.2, 435/240.2, 320.1, 357; 530/350

[56] References Cited

U.S. PATENT DOCUMENTS 4,797,368   1/1989   Carter et al. .................... 435/320
5,166,066  11/1992   Carter ............................ 435/240.2

OTHER PUBLICATIONS

Ymer et al. "GABA-A Receptor Beta Subunit Heterogeneity: Functional Expression fo Cloned cDNAs", The EMBO Journal, vol. 8 No. 6 pp. 1665-1670 (1989).

Levitan et al. "Structural and Functional Basis for GABA-A Receptor Heterogeneity", Nature, Vo.. 335, No. 1 (9/88).

Luddens et al., "Cerebeller GABA-A Receptor Selective for a Behavioral Alcohol Antagonists", Nature, vol. 346, No. 16(8/90).

Malherbe et al. "Functional expression and sites of gene transcription of a novel alpha subunit of the GABA-A receptor in rat brain", FEBS Letters, vol. 260, pp. 261-265 (1990).

Sunbrook et al. "Synthetic Oligonucleotide Probes", Cold Springs Harbor, NY, Press, Chapter 12 (selected pages) 1989.

Whiting et al. "Another mechanism for creating diversity in the Gamma-aminobutyrate type A receptors: RNA splicing . . . ", Proc. Natl. Acad. Sci, vol. 87 pp. 9966-9970 (1990).

Pritchett et al. "Importance of novel GABA-A receptor subunit for benzodiazephine pharmacology", Nature, vol. 338, pp. 582-585 (1989).

Kleingoor et al. "Inverse but not full benzodiazepine agonists modulate recombinant alpha-6, beta-2, gamma-2 GABA-A receptors . . . ", Neuroscience Letters, vol. 130, pp. 169-172 (1991).

Moss et al., "Cloned GABA receptors are maintained in a stable cell line: allosteric and channel properties", Eur. Jour. of Pharma., vol. 189, pp. 77-88 (1990).

Schofield et al. "Sequence and expression of human GABA-A receptor alpha-1 and beta-1 subunits", FEBS Letters, vol. 244, No. 2, pp. 361-364 (1989).

Primary Examiner—John Ulm
Attorney, Agent, or Firm—Michael D. Yablonsky; J. Mark Hand; Jack L. Tribble

[57] ABSTRACT

The present invention relates to a stably co-transfected eukaryotic cell line capable of expressing a GABA-A receptor, particularly a human GABA-A receptor, which receptor comprises at least one alpha, one beta and one gamma subunit; to the cloning of novel cDNA sequences encoding the $\alpha$-2, $\alpha$-3, $\alpha$-5, $\alpha$-6 and $\beta$-2 subunits of the human GABA-A receptor; and to the use of the cell line in designing and developing GABA-A receptor subtype-selective medicaments.

16 Claims, 17 Drawing Sheets

```
CCTAGCGCTC CTCTCCGGCT TCCACCAGCC CATCGCTCCA CGCTCTCTTG GCTGCTGCAG      60
TCTCGGTCTC TCTCTCTCTC TCTCTCTCTC TCTCTCTCTC TCTCTCTCTC TCTCTCTCTC     120
TCTCTCTCTC TCTCTCCCAA GTTTCCTATC TCGTCAAGAT CAGGGCAAAA GAAGAAAACA     180
CCGAATTCTG CTTGCCGTTT CAGAGCGGCG GTG ATG AAG ACA AAA TTG AAC ATC     234
                                    Met Lys Thr Lys Leu Asn Ile
                                     1               5
```

```
TAC AAC ATC GAG TTC CTG CTT TTT GTT TTC TTG GTG TGG GAC CCT GCC     282
Tyr Asn Ile Glu Phe Leu Leu Phe Val Phe Leu Val Trp Asp Pro Ala
            10              15              20

AGG TTG GTG CTG GCT AAC ATC CAA GAA GAT GAG GCT AAA AAT AAC ATT     330
Arg Leu Val Leu Ala Asn Ile Gln Glu Asp Glu Ala Lys Asn Asn Ile
    25              30              35

ACC ATC TTT ACG AGA ATT CTT GAC AGA CTT CTG GAT GGT TAC GAT AAT     378
Thr Ile Phe Thr Arg Ile Leu Asp Arg Leu Leu Asp Gly Tyr Asp Asn
40              45              50              55

CGG CTT AGA CCA GGA CTG GGA GAC AGT ATT ACT GAA GTC TTC ACT AAC     426
Arg Leu Arg Pro Gly Leu Gly Asp Ser Ile Thr Glu Val Phe Thr Asn
                60              65              70

ATC TAC GTG ACC AGT TTT GGC CCT GTC TCA GAT ACA GAT ATG GAA TAT     474
Ile Tyr Val Thr Ser Phe Gly Pro Val Ser Asp Thr Asp Met Glu Tyr
            75              80              85

ACA ATT GAT GTT TTC TTT CGA CAA AAA TGG AAA GAT GAA CGT TTA AAA     522
Thr Ile Asp Val Phe Phe Arg Gln Lys Trp Lys Asp Glu Arg Leu Lys
        90              95              100

TTT AAA GGT CCT ATG AAT ATC CTT CGA CTA AAC AAT TTA ATG GCT AGC     570
Phe Lys Gly Pro Met Asn Ile Leu Arg Leu Asn Asn Leu Met Ala Ser
    105             110             115

AAA ATC TGG ACT CCA GAT ACC TTT TTT CAC AAT GGG AAG AAA TCA GTA     618
Lys Ile Trp Thr Pro Asp Thr Phe Phe His Asn Gly Lys Lys Ser Val
120             125             130             135

GCT CAT AAT ATG ACA ATG CCA AAT AAG TTG CTT CGA ATT CAG GAT GAT     666
Ala His Asn Met Thr Met Pro Asn Lys Leu Leu Arg Ile Gln Asp Asp
                140             145             150
```

FIG.2A

| | | | | | | | | | | | | | | | |
|---|---|---|---|---|---|---|---|---|---|---|---|---|---|---|---|
| GGG | ACT | CTG | CTG | TAT | ACC | ATG | AGG | CTT | ACA | GTT | CAA | GCT | GAA | TGC | CCA | 714
| Gly | Thr | Leu | Leu | Tyr | Thr | Met | Arg | Leu | Thr | Val | Gln | Ala | Glu | Cys | Pro |
| | | | 155 | | | | | 160 | | | | | 165 | | |

```
GGG ACT CTG CTG TAT ACC ATG AGG CTT ACA GTT CAA GCT GAA TGC CCA    714
Gly Thr Leu Leu Tyr Thr Met Arg Leu Thr Val Gln Ala Glu Cys Pro
            155             160             165

ATG CAC TTG GAG GAT TTC CCA ATG GAT GCT CAT TCA TGT CCT CTG AAA    762
Met His Leu Glu Asp Phe Pro Met Asp Ala His Ser Cys Pro Leu Lys
            170             175             180

TTT GGC AGC TAT GCA TAT ACA ACT TCA GAG GTC ACT TAT ATT TGG ACT    810
Phe Gly Ser Tyr Ala Tyr Thr Thr Ser Glu Val Thr Tyr Ile Trp Thr
            185             190             195

TAC AAT GCA TCT GAT TCA GTA CAG GTT GCT CCT GAT GGC TCT AGG TTA    858
Tyr Asn Ala Ser Asp Ser Val Gln Val Ala Pro Asp Gly Ser Arg Leu
200             205             210             215

AAT CAA TAT GAC CTG CTG GGC CAA TCA ATC GGA AAG GAG ACA ATT AAA    906
Asn Gln Tyr Asp Leu Leu Gly Gln Ser Ile Gly Lys Glu Thr Ile Lys
            220             225             230

TCC AGT ACA GGT GAA TAT ACT GTA ATG ACA GCT CAT TTC CAC CTG AAA    954
Ser Ser Thr Gly Glu Tyr Thr Val Met Thr Ala His Phe His Leu Lys
            235             240             245

AGA AAA ATT GGG TAT TTT GTG ATT CAA ACC TAT CTG CCT TGC ATC ATG    1002
Arg Lys Ile Gly Tyr Phe Val Ile Gln Thr Tyr Leu Pro Cys Ile Met
            250             255             260

ACT GTC ATT CTC TCC CAA GTT TCA TTC TGG CTT AAC AGA GAA TCT GTG    1050
Thr Val Ile Leu Ser Gln Val Ser Phe Trp Leu Asn Arg Glu Ser Val
            265             270             275

CCT GCA AGA ACT GTG TTT GGA GTA ACA ACT GTC CTA ACA ATG ACA ACT    1098
Pro Ala Arg Thr Val Phe Gly Val Thr Thr Val Leu Thr Met Thr Thr
280             285             290             295

CTA AGC ATC AGT GCT CGG AAT TCT CTC CCC AAA GTG GCT TAT GCA ACT    1146
Leu Ser Ile Ser Ala Arg Asn Ser Leu Pro Lys Val Ala Tyr Ala Thr
            300             305             310

GCC ATG GAC TGG TTT ATT GCT GTT TGT TAT GCA TTT GTG TTC TCT GCC    1194
Ala Met Asp Trp Phe Ile Ala Val Cys Tyr Ala Phe Val Phe Ser Ala
            315             320             325
```

FIG.2B

| | | | | | | | | | | | | | | | |
|---|---|---|---|---|---|---|---|---|---|---|---|---|---|---|---|
| CTA | ATT | GAA | TTT | GCA | ACT | GTT | AAT | TAC | TTC | ACC | AAA | AGA | GGA | TGG | ACT | 1242
| Leu | Ile | Glu | Phe | Ala | Thr | Val | Asn | Tyr | Phe | Thr | Lys | Arg | Gly | Trp | Thr |
|  |  | 330 |  |  |  | 335 |  |  |  |  | 340 |  |  |  |  |

```
CTA ATT GAA TTT GCA ACT GTT AAT TAC TTC ACC AAA AGA GGA TGG ACT   1242
Leu Ile Glu Phe Ala Thr Val Asn Tyr Phe Thr Lys Arg Gly Trp Thr
        330             335                 340

TGG GAT GGG AAG AGT GTA GTA AAT GAC AAG AAA AAA GAA AAG GCT TCC   1290
Trp Asp Gly Lys Ser Val Val Asn Asp Lys Lys Lys Glu Lys Ala Ser
        345             350                 355

GTT ATG ATA CAG AAC AAC GCT TAT GCA GTG GCT GTT GCC AAT TAT GCC   1338
Val Met Ile Gln Asn Asn Ala Tyr Ala Val Ala Val Ala Asn Tyr Ala
360             365                 370                 375

CCG AAT CTT TCA AAA GAT CCA GTT CTC TCC ACC ATC TCC AAG AGT GCA   1386
Pro Asn Leu Ser Lys Asp Pro Val Leu Ser Thr Ile Ser Lys Ser Ala
            380             385                 390

ACC ACG CCA GAA CCC AAC AAG AAG CCA GAA AAC AAG CCA GCT GAA GCA   1434
Thr Thr Pro Glu Pro Asn Lys Lys Pro Glu Asn Lys Pro Ala Glu Ala
            395             400                 405

AAG AAA ACT TTC AAC AGT GTT AGC AAA ATT GAC AGA ATG TCC AGA ATA   1482
Lys Lys Thr Phe Asn Ser Val Ser Lys Ile Asp Arg Met Ser Arg Ile
        410             415                 420

GTT TTT CCA GTT TTG TTT GGT ACC TTT AAT TTA GTT TAC TGG GCT ACA   1530
Val Phe Pro Val Leu Phe Gly Thr Phe Asn Leu Val Tyr Trp Ala Thr
        425             430                 435
                                                    >
TAT TTA AAC AGA GAA CCT GTA TTA GGG GTC AGT CCT TGAATTGAGA CCCATG 1582
Tyr Leu Asn Arg Glu Pro Val Leu Gly Val Ser Pro
440             445             450

TTATCTTTGG GATGTATAGC AACATTAAAT TTGGTTTGTT TTGCTATGTA CAGTCTGACT  1642

AATAACTGCT AATTTGTGAT CCAACATGTA CAGTATGTAT ATAGTGACAT AGCTTACCAG  1702

TAGACCTTTA ATGGAGACAT GCATTTGCTA ACTCATGGAA CTGCAGACAG AAAGCACTCC  1762

ATGCGAAAAC AGCCATTGCC TTTTTTAAAG ATTTACCCTA GGACCTGATT TAAAGTGAAT  1822

TTCAAGTGAC CTGATTAATT TCCTATTCTT CCAAATGAGA TGAAAATGGG GATCCTGTAC  1882

AACCCTTTGT GGACCCTTTT GGTTTAGCTC TTAAGTAGGG GTATTTTCTA CTGTTGCTTA  1942
```

FIG. 2C

```
ATTATGATGG AAGATAACAT TGTCATTCCT AGATGAATCC TTTGAAGTAA CAAACATTGT    2002

ATCTGACATC AGCTCTGTTC ATGAGTGCTC AGAGTCCCTG CTAATGTAAT TGGAAGCTTG    2062

GTACACATAA GAAAAACTAG AGATTTGAAA TCTAGCTATG AATTACTCTA TATAGTATCT    2122

ATAGCCATGT ACATATTACA GCATGACAAG CTCGAAATAA TTATGAGTCA GCCCGAAAGA    2182

TGTTAATTA                                                            2191
```

FIG. 2D

```
GAATTCCCTT GTTTCAGTTC ATTCATCCTT CTCTCCTTTC CGCTCAGACT GTAGAGCTCG        60
GTCTCTCCAA GTTTGTGCCT AAGAAG ATG ATA ATC ACA CAA ACA AGT CAC TGT       113
                             Met Ile Ile Thr Gln Thr Ser His Cys
                              1               5

TAC ATG ACC AGC CTT GGG ATT CTT TTC CTG ATT AAT ATT CTC CCT GGA        161
Tyr Met Thr Ser Leu Gly Ile Leu Phe Leu Ile Asn Ile Leu Pro Gly
 10              15                  20                  25

ACC ACT GGT CAA GGG GAA TCA AGA CGA CAA GAA CCC GGG GAC TTT GTG        209
Thr Thr Gly Gln Gly Glu Ser Arg Arg Gln Glu Pro Gly Asp Phe Val
             30                  35                  40

AAG CAG GAC ATT GGC GGG CTG TCT CCT AAG CAT GCC CCA GAT ATT CCT        257
Lys Gln Asp Ile Gly Gly Leu Ser Pro Lys His Ala Pro Asp Ile Pro
             45                  50                  55

GAT GAC AGC ACT GAC AAC ATC ACT ATC TTC ACC AGA ATC TTG GAT CGT        305
Asp Asp Ser Thr Asp Asn Ile Thr Ile Phe Thr Arg Ile Leu Asp Arg
             60                  65                  70

CTT CTG GAC GGC TAT GAC AAC CGG CTG CGA CCT GGG CTT GGA GAT GCA        353
Leu Leu Asp Gly Tyr Asp Asn Arg Leu Arg Pro Gly Leu Gly Asp Ala
     75                  80                  85

GTG ACT GAA GTG AAG ACT GAC ATC TAC GTG ACC AGT TTT GGC CCT GTG        401
Val Thr Glu Val Lys Thr Asp Ile Tyr Val Thr Ser Phe Gly Pro Val
 90              95                 100                 105

TCA GAC ACT GAC ATG GAG TAC ACT ATT GAT GTA TTT TTT CGG CAG ACA        449
Ser Asp Thr Asp Met Glu Tyr Thr Ile Asp Val Phe Phe Arg Gln Thr
                110                 115                 120

TGG CAT GAT GAA AGA CTG AAA TTT GAT GGC CCC ATG AAG ATC CTT CCA        497
Trp His Asp Glu Arg Leu Lys Phe Asp Gly Pro Met Lys Ile Leu Pro
             125                 130                 135

CTG AAC AAT CTC CTG GCT AGT AAG ATC TGG ACA CCG GAC ACC TTC TTC        545
Leu Asn Asn Leu Leu Ala Ser Lys Ile Trp Thr Pro Asp Thr Phe Phe
             140                 145                 150

CAC AAT GGC AAG AAA TCA GTG GCT CAT AAC ATG ACC ACG CCC AAC AAG        593
His Asn Gly Lys Lys Ser Val Ala His Asn Met Thr Thr Pro Asn Lys
             155                 160                 165

CTG CTC AGA TTG GTG GAC AAC GGA ACC CTC CTC TAT ACA ATG AGG TTA        641
Leu Leu Arg Leu Val Asp Asn Gly Thr Leu Leu Tyr Thr Met Arg Leu
 170                 175                 180                 185
```

FIG.3A

```
ACA ATT CAT GCT GAG TGT CCC ATG CAT TTG GAA GAT TTT CCC ATG GAT    689
Thr Ile His Ala Glu Cys Pro Met His Leu Glu Asp Phe Pro Met Asp
            190             195             200

GTG CAT GCC TGC CCA CTG AAG TTT GGA AGC TAT GCC TAT ACA ACA GCT    737
Val His Ala Cys Pro Leu Lys Phe Gly Ser Tyr Ala Tyr Thr Thr Ala
        205             210             215

GAA GTG GTT TAT TCT TGG ACT CTC GGA AAG AAC AAA TCC GTG GAA GTG    785
Glu Val Val Tyr Ser Trp Thr Leu Gly Lys Asn Lys Ser Val Glu Val
        220             225             230

GCA CAG GAT GGT TCT CGC TTG AAC CAG TAT GAC CTT TTG GGC CAT GTT    833
Ala Gln Asp Gly Ser Arg Leu Asn Gln Tyr Asp Leu Leu Gly His Val
        235             240             245

GTT GGG ACA GAG ATA ATC CGG TCT AGT ACA GGA GAA TAT GTC GTC ATG    881
Val Gly Thr Glu Ile Ile Arg Ser Ser Thr Gly Glu Tyr Val Val Met
250             255             260             265

ACA ACC CAC TTC CAT CTC AAG CGA AAA ATT GGC TAC TTT GTG ATC CAG    929
Thr Thr His Phe His Leu Lys Arg Lys Ile Gly Tyr Phe Val Ile Gln
                270             275             280

ACC TAC TTG CCA TGT ATC ATG ACT GTC ATT CTG TCA CAA GTG TCG TTC    977
Thr Tyr Leu Pro Cys Ile Met Thr Val Ile Leu Ser Gln Val Ser Phe
            285             290             295

TGG CTC AAC AGA GAG TCT GTT CCT GCC CGT ACA GTC TTT GGT GTC ACC    1025
Trp Leu Asn Arg Glu Ser Val Pro Ala Arg Thr Val Phe Gly Val Thr
        300             305             310

ACT GTG CTT ACC ATG ACC ACC TTG AGT ATC AGT GCC AGA AAT TCC TTA    1073
Thr Val Leu Thr Met Thr Thr Leu Ser Ile Ser Ala Arg Asn Ser Leu
        315             320             325

CCT AAA GTG GCA TAT GCG ACG GCC ATG GAC TGG TTC ATA GCC GTC TGT    1121
Pro Lys Val Ala Tyr Ala Thr Ala Met Asp Trp Phe Ile Ala Val Cys
330             335             340             345

TAT GCC TTT GTA TTT TCT GCA CTG ATT GAA TTT GCC ACT GTC AAC TAT    1169
Tyr Ala Phe Val Phe Ser Ala Leu Ile Glu Phe Ala Thr Val Asn Tyr
                350             355             360

TTC ACC AAG CGG AGT TGG GCT TGG GAA GGC AAG AAG GTG CCA GAG GCC    1217
Phe Thr Lys Arg Ser Trp Ala Trp Glu Gly Lys Lys Val Pro Glu Ala
            365             370             375
```

FIG.3B

```
CTG GAG ATG AAG AAG AAA ACA CCA GCA GCC CCA GCA AAG AAA ACC AGC    1265
Leu Glu Met Lys Lys Lys Thr Pro Ala Ala Pro Ala Lys Lys Thr Ser
        380             385             390

ACT ACC TTC AAC ATC GTG GGG ACC ACC TAT CCC ATC AAC CTG GCC AAG    1313
Thr Thr Phe Asn Ile Val Gly Thr Thr Tyr Pro Ile Asn Leu Ala Lys
    395             400             405

GAC ACT GAA TTT TCC ACC ATC TCC AAG GGC GCT GCT CCC AGT GCC TCC    1361
Asp Thr Glu Phe Ser Thr Ile Ser Lys Gly Ala Ala Pro Ser Ala Ser
410             415             420             425

TCA ACC CCA ACA ATC ATT GCT TCA CCC AAG GCC ACC TAC GTG CAG GAC    1409
Ser Thr Pro Thr Ile Ile Ala Ser Pro Lys Ala Thr Tyr Val Gln Asp
            430             435             440

AGC CCG ACT GAG ACC AAG ACC TAC AAC AGT GTC AGC AAG GTT GAC AAA    1457
Ser Pro Thr Glu Thr Lys Thr Tyr Asn Ser Val Ser Lys Val Asp Lys
            445             450             455

ATT TCC CGC ATC ATC TTT CCT GTG CTC TTT GCC ATA TTC AAT CTG GTC    1505
Ile Ser Arg Ile Ile Phe Pro Val Leu Phe Ala Ile Phe Asn Leu Val
        460             465             470

TAT TGG GCC ACA TAT GTC AAC CGG GAG TCA GCT ATC AAG GGC ATG ATC    1553
Tyr Trp Ala Thr Tyr Val Asn Arg Glu Ser Ala Ile Lys Gly Met Ile
    475             480             485

CGC AAA CAG TAGATAGTGG CAGTGCAGCA ACCAGAGCAC TGTATACCCC GTGAAGCATC 1612
Arg Lys Gln                                                        490

CAGGCACCCA AACCCCGGGG CTCCCC                                       1638
```

FIG.3C

```
GAATTCCCCC CTTGCAGGCC GAGCCGGGGC CCTGCGCCCT CCCCCTCCGC CCAGCTCGGC    60
CAAGGCCGCA TTTGCTGAGC GTCTGGCGGC CTCTACCGGA GCACCTCTGC AGAGGGCCCA   120
TCCTCCAGCC CAGAGACGAC ATGTGGCGCT CGGGCGAGTG CCTTGCAGAG AGAGGAGTAG   180
CTTGCTGGCT TTGAACGCGT GGCGTGGCAG ATATTTCAGA AAGCTTCAAG AACAAGCTGG   240
                                                              >
AGAAGGGAAG AGTTATTCCT CCATATTCAC CTGCTTCAAC TACTATTCTT ATTGGGA ATG  300
                                                              Met
                                                               1
```

| GAC | AAT | GGA | ATG | TTC | TCT | GGT | TTT | ATC | ATG | ATC | AAA | AAC | CTC | CTT | CTC | 348 |
|-----|-----|-----|-----|-----|-----|-----|-----|-----|-----|-----|-----|-----|-----|-----|-----|-----|
| Asp | Asn | Gly | Met | Phe | Ser | Gly | Phe | Ile | Met | Ile | Lys | Asn | Leu | Leu | Leu | |
|     |     |  5  |     |     |     |     |     |  10 |     |     |     |     |  15 |     |     | |

| TTT | TGT | ATT | TCC | ATG | AAC | TTA | TCC | AGT | CAC | TTT | GGC | TTT | TCA | CAG | ATG | 396 |
|-----|-----|-----|-----|-----|-----|-----|-----|-----|-----|-----|-----|-----|-----|-----|-----|-----|
| Phe | Cys | Ile | Ser | Met | Asn | Leu | Ser | Ser | His | Phe | Gly | Phe | Ser | Gln | Met | |
|     |     | 20  |     |     |     |     |  25 |     |     |     |     |  30 |     |     |     | |

| CCA | ACC | AGT | TCA | GTG | AAA | GAT | GAG | ACC | AAT | GAC | AAC | ATC | ACG | ATA | TTT | 444 |
|-----|-----|-----|-----|-----|-----|-----|-----|-----|-----|-----|-----|-----|-----|-----|-----|-----|
| Pro | Thr | Ser | Ser | Val | Lys | Asp | Glu | Thr | Asn | Asp | Asn | Ile | Thr | Ile | Phe | |
|     |     | 35  |     |     |     |  40 |     |     |     |     |  45 |     |     |     |     | |

| ACC | AGG | ATC | TTG | GAT | GGG | CTC | TTG | GAT | GGC | TAC | GAC | AAC | AGA | CTT | CGG | 492 |
|-----|-----|-----|-----|-----|-----|-----|-----|-----|-----|-----|-----|-----|-----|-----|-----|-----|
| Thr | Arg | Ile | Leu | Asp | Gly | Leu | Leu | Asp | Gly | Tyr | Asp | Asn | Arg | Leu | Arg | |
| 50  |     |     |     |     |  55 |     |     |     |     |  60 |     |     |     |     |  65 | |

| CCC | GGG | CTG | GGA | GAG | CGC | ATC | ACT | CAG | GTG | AGG | ACC | GAC | ATC | TAC | GTC | 540 |
|-----|-----|-----|-----|-----|-----|-----|-----|-----|-----|-----|-----|-----|-----|-----|-----|-----|
| Pro | Gly | Leu | Gly | Glu | Arg | Ile | Thr | Gln | Val | Arg | Thr | Asp | Ile | Tyr | Val | |
|     |     |     |  70 |     |     |     |     |  75 |     |     |     |     |  80 |     |     | |

| ACC | AGC | TTC | GGC | CCG | GTG | TCC | GAC | ACG | GAA | ATG | GAG | TAC | ACC | ATA | GAC | 588 |
|-----|-----|-----|-----|-----|-----|-----|-----|-----|-----|-----|-----|-----|-----|-----|-----|-----|
| Thr | Ser | Phe | Gly | Pro | Val | Ser | Asp | Thr | Glu | Met | Glu | Tyr | Thr | Ile | Asp | |
|     |     |     |  85 |     |     |     |     |  90 |     |     |     |     |  95 |     |     | |

| GTG | TTT | TTC | CGA | CAA | AGC | TGG | AAA | GAT | GAA | AGG | CTT | CGG | TTT | AAG | GGG | 636 |
|-----|-----|-----|-----|-----|-----|-----|-----|-----|-----|-----|-----|-----|-----|-----|-----|-----|
| Val | Phe | Phe | Arg | Gln | Ser | Trp | Lys | Asp | Glu | Arg | Leu | Arg | Phe | Lys | Gly | |
|     |     | 100 |     |     |     |     | 105 |     |     |     |     | 110 |     |     |     | |

| CCC | ATG | CAG | CGC | CTC | CCT | CTC | AAC | AAC | CTC | CTT | GCC | AGC | AAG | ATC | TGG | 684 |
|-----|-----|-----|-----|-----|-----|-----|-----|-----|-----|-----|-----|-----|-----|-----|-----|-----|
| Pro | Met | Gln | Arg | Leu | Pro | Leu | Asn | Asn | Leu | Leu | Ala | Ser | Lys | Ile | Trp | |
|     | 115 |     |     |     |     | 120 |     |     |     |     | 125 |     |     |     |     | |

| ACC | CCA | GAC | ACG | TTC | TTC | CAC | AAC | GGG | AAG | AAG | TCC | ATC | GCT | CAC | AAC | 732 |
|-----|-----|-----|-----|-----|-----|-----|-----|-----|-----|-----|-----|-----|-----|-----|-----|-----|
| Thr | Pro | Asp | Thr | Phe | Phe | His | Asn | Gly | Lys | Lys | Ser | Ile | Ala | His | Asn | |
| 130 |     |     |     |     | 135 |     |     |     |     | 140 |     |     |     |     | 145 | |

| ATG | ACC | ACG | CCC | AAC | AAG | CTG | CTG | CGG | CTG | GAG | GAC | GAC | GGC | ACC | CTG | 780 |
|-----|-----|-----|-----|-----|-----|-----|-----|-----|-----|-----|-----|-----|-----|-----|-----|-----|
| Met | Thr | Thr | Pro | Asn | Lys | Leu | Leu | Arg | Leu | Glu | Asp | Asp | Gly | Thr | Leu | |
|     |     |     |     | 150 |     |     |     |     | 155 |     |     |     |     | 160 |     | |

FIG.4A

| | | | | | | | | | | | | | | |
|---|---|---|---|---|---|---|---|---|---|---|---|---|---|---|
| CTC | TAC | ACC | ATG | CGC | TTG | ACC | ATC | TCT | GCA | GAG | TGC | CCC | ATG | CAG | CTT | 828 |
| Leu | Tyr | Thr | Met | Arg | Leu | Thr | Ile | Ser | Ala | Glu | Cys | Pro | Met | Gln | Leu | |
| | | | 165 | | | | 170 | | | | | 175 | | | | |

| GAG | GAC | TTC | CCG | ATG | GAT | GCG | CAC | GCT | TGC | CCT | CTG | AAA | TTT | GGC | AGC | 876 |
| Glu | Asp | Phe | Pro | Met | Asp | Ala | His | Ala | Cys | Pro | Leu | Lys | Phe | Gly | Ser | |
| | | 180 | | | | | 185 | | | | | 190 | | | | |

| TAT | GCG | TAC | CCT | AAT | TCT | GAA | GTC | GTT | TAC | GTC | TGG | ACC | AAC | GGC | TCC | 924 |
| Tyr | Ala | Tyr | Pro | Asn | Ser | Glu | Val | Val | Tyr | Val | Trp | Thr | Asn | Gly | Ser | |
| | 195 | | | | | 200 | | | | | 205 | | | | | |

| ACC | AAG | TCG | GTG | GTG | GTG | GCG | GAA | GAT | GGC | TCC | AGA | CTG | AAC | CAG | TAC | 972 |
| Thr | Lys | Ser | Val | Val | Val | Ala | Glu | Asp | Gly | Ser | Arg | Leu | Asn | Gln | Tyr | |
| 210 | | | | | 215 | | | | 220 | | | | | 225 | | |

| CAC | CTG | ATG | GGG | CAG | ACG | GTG | GGC | ACT | GAG | AAC | ATC | AGC | ACC | AGC | ACA | 1020 |
| His | Leu | Met | Gly | Gln | Thr | Val | Gly | Thr | Glu | Asn | Ile | Ser | Thr | Ser | Thr | |
| | | | | 230 | | | | | 235 | | | | 240 | | | |

| GGC | GAA | TAC | ACA | ATC | ATG | ACA | GCT | CAC | TTC | CAC | CTG | AAA | AGG | AAG | ATT | 1068 |
| Gly | Glu | Tyr | Thr | Ile | Met | Thr | Ala | His | Phe | His | Leu | Lys | Arg | Lys | Ile | |
| | | | 245 | | | | | 250 | | | | | 255 | | | |

| GGC | TAC | TTT | GTC | ATC | CAG | ACC | TAC | CTT | CCC | TGC | ATA | ATG | ACC | GTG | ATC | 1116 |
| Gly | Tyr | Phe | Val | Ile | Gln | Thr | Tyr | Leu | Pro | Cys | Ile | Met | Thr | Val | Ile | |
| | | | 260 | | | | | 265 | | | | | 270 | | | |

| TTA | TCA | CAG | GTG | TCC | TTT | TGG | CTG | AAC | CGG | GAA | TCA | GTC | CCA | GCC | AGG | 1164 |
| Leu | Ser | Gln | Val | Ser | Phe | Trp | Leu | Asn | Arg | Glu | Ser | Val | Pro | Ala | Arg | |
| | 275 | | | | | 280 | | | | | 285 | | | | | |

| ACA | GTT | TTT | GGG | GTC | ACC | ACG | GTG | CTG | ACC | ATG | ACG | ACC | CTC | AGC | ATC | 1212 |
| Thr | Val | Phe | Gly | Val | Thr | Thr | Val | Leu | Thr | Met | Thr | Thr | Leu | Ser | Ile | |
| 290 | | | | | 295 | | | | | 300 | | | | | 305 | |

| AGC | GCC | AGG | AAC | TCT | CTG | CCC | AAA | GTG | GCC | TAC | GCC | ACC | GCC | ATG | GAC | 1260 |
| Ser | Ala | Arg | Asn | Ser | Leu | Pro | Lys | Val | Ala | Tyr | Ala | Thr | Ala | Met | Asp | |
| | | | | 310 | | | | | 315 | | | | | 320 | | |

| TGG | TTC | ATA | GCT | GTG | TGC | TAT | GCC | TTC | GTC | TTC | TCG | GCG | CTG | ATA | GAG | 1308 |
| Trp | Phe | Ile | Ala | Val | Cys | Tyr | Ala | Phe | Val | Phe | Ser | Ala | Leu | Ile | Glu | |

FIG.4B

```
                    325                    330                         335
TTT GCC ACG GTC AAT TAC TTT ACC AAG AGA GGC TGG GCC TGG GAT GGC          1356
Phe Ala Thr Val Asn Tyr Phe Thr Lys Arg Gly Trp Ala Trp Asp Gly
        340                 345                 350

AAA AAA GCC TTG GAA GCA GCC AAG ATC AAG AAA AAG CGT GAA GTC ATA          1404
Lys Lys Ala Leu Glu Ala Ala Lys Ile Lys Lys Lys Arg Glu Val Ile
355                 360                 365

CTA AAT AAG TCA ACA AAC GCT TTT ACA ACT GGG AAG ATG TCT CAC CCC          1452
Leu Asn Lys Ser Thr Asn Ala Phe Thr Thr Gly Lys Met Ser His Pro
370                 375                 380                 385

CCA AAC ATT CCG AAG GAA CAG ACC CCA GCA GGG ACG TCG AAT ACA ACC          1500
Pro Asn Ile Pro Lys Glu Gln Thr Pro Ala Gly Thr Ser Asn Thr Thr
                390                 395                 400

TCA GTC TCA GTA AAA CCC TCT GAA GAG AAG ACT TCT GAA AGC AAA AAG          1548
Ser Val Ser Val Lys Pro Ser Glu Glu Lys Thr Ser Glu Ser Lys Lys
        405                 410                 415

ACT TAC AAC AGT ATC AGC AAA ATT GAC AAA ATG TCC CGA ATC GTA TTC          1596
Thr Tyr Asn Ser Ile Ser Lys Ile Asp Lys Met Ser Arg Ile Val Phe
        420                 425                 430

CCA GTC TTG TTC GGC ACT TTC AAC TTA GTT TAC TGG GCA ACG TAT TTG          1644
Pro Val Leu Phe Gly Thr Phe Asn Leu Val Tyr Trp Ala Thr Tyr Leu
        435                 440                 445
                                                      —>
AAT AGG GAG CCG GTG ATA AAA GGA GCC GCC TCT CCA AAA TAACCGGCCA CAC       1696
Asn Arg Glu Pro Val Ile Lys Gly Ala Ala Ser Pro Lys
450                 455                 460

TCCCAAACTC CAAGACAGCC ATACTTCCAG CGAAATGGTA CCAAGGAGAG GTTTTGCTCA        1756
CAGGGACTCT CCATATGTGA GCACTATCTT TCAGGAAATT TTTGCATGTT TAATAATATG       1816
TACAAATAAT ATTGCCTTGA TGTTTCTATA TGTAACTTCA GATGTTTCCA AGATGTCCCA       1876
TTGATAATTC GAGCAAACAA CTTTCTGGAA AAACAGGATA CGATGACTGA CACTCAGATG       1936
CCCAGTATCA TACGTTGATA GTTACAAAC  AAGATACGTA TATTTTAAC  TGCTTCAAGT       1996
GTTACCTAAC AATGTTTTTT ATACTTCAAA TGTCATTTCA TACAAATTTT CCCAGTGAAT       2056
AAATATTTTA GGAAACTCTC CATGATTATT AGAAGACCAA CTATATTGCC AGAAACAGAG       2116
ATCATAAAGA GCACGTTTTC CATTATGAGG AAACTTGGAC ATTTATGTAC AAAATGAATT       2176
GCCTTTGATA ATTCTTACTG TTCTGAAATT AGGAAAGTAC TTGCATGATC TTACACGAAG       2236
AAATAGAATA GGCAAACTTT TATGTAGCCA GATTAATAAC AGAAATACAT CATATGTTAG       2296
ATACACAAAA TATT                                                         2310
```

FIG.4C

```
AATTCTGCAT TTCAGTGCAC TGCAGG ATG GCG TCA TCT CTG CCC TGG CTG TGC    53
              Met Ala Ser Ser Leu Pro Trp Leu Cys
               1               5
```

| ATT | ATT | CTG | TGG | CTA | GAA | AAT | GCC | CTA | GGG | AAA | CTC | GAA | GTT | GAA | GGC | 101 |
| Ile | Ile | Leu | Trp | Leu | Glu | Asn | Ala | Leu | Gly | Lys | Leu | Glu | Val | Glu | Gly | |
| 10  |     |     |     |     | 15  |     |     |     |     | 20  |     |     |     |     | 25  | |

| AAC | TTC | TAC | TCA | GAA | AAC | GTC | AGT | CGG | ATC | CTG | GAC | AAC | TTG | CTT | GAA | 149 |
| Asn | Phe | Tyr | Ser | Glu | Asn | Val | Ser | Arg | Ile | Leu | Asp | Asn | Leu | Leu | Glu | |
|     |     |     |     | 30  |     |     |     |     | 35  |     |     |     |     | 40  |     | |

| GGC | TAT | GAC | AAT | CGG | CTG | CGG | CCG | GGA | TTT | GGA | GGT | GCT | GTC | ACT | GAA | 197 |
| Gly | Tyr | Asp | Asn | Arg | Leu | Arg | Pro | Gly | Phe | Gly | Gly | Ala | Val | Thr | Glu | |
|     |     |     | 45  |     |     |     |     | 50  |     |     |     |     | 55  |     |     | |

| GTC | AAA | ACA | GAC | ATT | TAT | GTG | ACC | AGT | TTT | GGG | CCC | GTG | TCA | GAT | GTG | 245 |
| Val | Lys | Thr | Asp | Ile | Tyr | Val | Thr | Ser | Phe | Gly | Pro | Val | Ser | Asp | Val | |
|     |     | 60  |     |     |     |     | 65  |     |     |     |     | 70  |     |     |     | |

| GAG | ATG | GAG | TAT | ACG | ATG | GAT | GTT | TTT | TTT | CGC | CAG | ACC | TGG | ACT | GAT | 293 |
| Glu | Met | Glu | Tyr | Thr | Met | Asp | Val | Phe | Phe | Arg | Gln | Thr | Trp | Thr | Asp | |
|     | 75  |     |     |     |     | 80  |     |     |     |     | 85  |     |     |     |     | |

| GAG | AGG | TTG | AAG | TTT | GGG | GGG | CCA | ACT | GAG | ATT | CTG | AGT | CTG | AAT | AAT | 341 |
| Glu | Arg | Leu | Lys | Phe | Gly | Gly | Pro | Thr | Glu | Ile | Leu | Ser | Leu | Asn | Asn | |
| 90  |     |     |     |     | 95  |     |     |     |     | 100 |     |     |     |     | 105 | |

| TTG | ATG | GTC | AGT | AAA | ATC | TGG | ACG | CCT | GAC | ACC | TTT | TTC | AGA | AAT | GGT | 389 |
| Leu | Met | Val | Ser | Lys | Ile | Trp | Thr | Pro | Asp | Thr | Phe | Phe | Arg | Asn | Gly | |
|     |     |     |     | 110 |     |     |     |     | 115 |     |     |     |     | 120 |     | |

| AAA | AAG | TCC | ATT | GCT | CAC | AAC | ATG | ACA | ACT | CCT | AAT | AAA | CTC | TTC | AGA | 437 |
| Lys | Lys | Ser | Ile | Ala | His | Asn | Met | Thr | Thr | Pro | Asn | Lys | Leu | Phe | Arg | |
|     |     |     | 125 |     |     |     |     | 130 |     |     |     |     | 135 |     |     | |

| ATA | ATG | CAG | AAT | GGA | ACC | ATT | TTA | TAC | ACC | ATG | AGG | CTT | ACC | ATC | AAT | 485 |
| Ile | Met | Gln | Asn | Gly | Thr | Ile | Leu | Tyr | Thr | Met | Arg | Leu | Thr | Ile | Asn | |
|     |     | 140 |     |     |     |     | 145 |     |     |     |     | 150 |     |     |     | |

| GCT | GAC | TGT | CCC | ATG | AGG | CTG | GTT | AAC | TTT | CCT | ATG | GAT | GGG | CAT | GCT | 533 |
| Ala | Asp | Cys | Pro | Met | Arg | Leu | Val | Asn | Phe | Pro | Met | Asp | Gly | His | Ala | |
|     | 155 |     |     |     |     | 160 |     |     |     |     | 165 |     |     |     |     | |

| TGT | CCA | CTC | AAG | TTT | GGG | AGC | TAT | GCT | TAT | CCC | AAA | AGT | GAA | ATC | ATA | 581 |
| Cys | Pro | Leu | Lys | Phe | Gly | Ser | Tyr | Ala | Tyr | Pro | Lys | Ser | Glu | Ile | Ile | |
| 170 |     |     |     |     | 175 |     |     |     |     | 180 |     |     |     |     | 185 | |

FIG.5A

| | | | | | | | | | | | | | | | |
|---|---|---|---|---|---|---|---|---|---|---|---|---|---|---|---|
| TAT | ACG | TGG | AAA | AAA | GGA | CCA | CTT | TAC | TCA | GTA | GAA | GTC | CCA | GAA | GAA | 629 |
| Tyr | Thr | Trp | Lys | Lys | Gly | Pro | Leu | Tyr | Ser | Val | Glu | Val | Pro | Glu | Glu |
| | | | 190 | | | | | 195 | | | | | 200 | | |
| TCT | TCA | AGC | CTT | CTC | CAG | TAT | GAT | CTG | ATT | GGA | CAA | ACA | GTA | TCT | AGT | 677 |
| Ser | Ser | Ser | Leu | Leu | Gln | Tyr | Asp | Leu | Ile | Gly | Gln | Thr | Val | Ser | Ser |
| | | | 205 | | | | | 210 | | | | | 215 | | |
| GAG | ACA | ATT | AAA | TCT | AAC | ACA | GGT | GAA | TAC | GTT | ATA | ATG | ACA | GTT | TAC | 725 |
| Glu | Thr | Ile | Lys | Ser | Asn | Thr | Gly | Glu | Tyr | Val | Ile | Met | Thr | Val | Tyr |
| | | 220 | | | | | 225 | | | | | 230 | | | |
| TTC | CAC | TTG | CAA | AGG | AAG | ATG | GGC | TAC | TTC | ATG | ATA | CAG | ATA | TAC | ACT | 773 |
| Phe | His | Leu | Gln | Arg | Lys | Met | Gly | Tyr | Phe | Met | Ile | Gln | Ile | Tyr | Thr |
| | 235 | | | | 240 | | | | | 245 | | | | | |
| CCT | TGC | ATT | ATG | ACA | GTC | ATT | CTT | TCC | CAG | GTG | TCT | TTC | TGG | ATT | AAT | 821 |
| Pro | Cys | Ile | Met | Thr | Val | Ile | Leu | Ser | Gln | Val | Ser | Phe | Trp | Ile | Asn |
| 250 | | | | | 255 | | | | | 260 | | | | | 265 |
| AAG | GAG | TCC | GTC | CCA | GCA | AGA | ACT | GTT | CTT | GGG | ATC | ACC | ACT | GTT | TTA | 869 |
| Lys | Glu | Ser | Val | Pro | Ala | Arg | Thr | Val | Leu | Gly | Ile | Thr | Thr | Val | Leu |
| | | | | 270 | | | | | 275 | | | | | 280 | |
| ACT | ATG | ACC | ACT | TTG | AGC | ATC | AGT | GCC | CGG | CAC | TCT | TTG | CCA | AAA | GTG | 917 |
| Thr | Met | Thr | Thr | Leu | Ser | Ile | Ser | Ala | Arg | His | Ser | Leu | Pro | Lys | Val |
| | | | 285 | | | | | 290 | | | | | 295 | | |
| TCA | TAT | GCC | ACT | GCC | ATG | GAT | TGG | TTC | ATA | GCT | GTT | TGC | TTT | GCA | TTC | 965 |
| Ser | Tyr | Ala | Thr | Ala | Met | Asp | Trp | Phe | Ile | Ala | Val | Cys | Phe | Ala | Phe |
| | | 300 | | | | | 305 | | | | | 310 | | | |
| GTC | TTC | TCT | GCT | CTT | ATC | GAG | TTC | GCA | GCT | GTC | AAC | TAC | TTT | ACC | AAT | 1013 |
| Val | Phe | Ser | Ala | Leu | Ile | Glu | Phe | Ala | Ala | Val | Asn | Tyr | Phe | Thr | Asn |
| | 315 | | | | | 320 | | | | | 325 | | | | |
| CTT | CAG | ACA | CAG | AAG | GCG | AAA | AGG | AAG | GCA | CAG | TTT | GCA | GCC | CCA | CCC | 1061 |
| Leu | Gln | Thr | Gln | Lys | Ala | Lys | Arg | Lys | Ala | Gln | Phe | Ala | Ala | Pro | Pro |
| 330 | | | | | 335 | | | | | 340 | | | | | 345 |
| ACA | GTG | ACA | ATA | TCA | AAA | GCT | ACT | GAA | CCT | TTG | GAA | GCT | GAG | ATT | GTT | 1109 |
| Thr | Val | Thr | Ile | Ser | Lys | Ala | Thr | Glu | Pro | Leu | Glu | Ala | Glu | Ile | Val |
| | | | | 350 | | | | | 355 | | | | | 360 | |
| TTG | CAT | CCT | GAC | TCC | AAA | TAT | CAT | CTG | AAG | AAA | AGG | ATC | ACT | TCT | CTG | 1157 |
| Leu | His | Pro | Asp | Ser | Lys | Tyr | His | Leu | Lys | Lys | Arg | Ile | Thr | Ser | Leu |
| | | | 365 | | | | | 370 | | | | | 375 | | |

FIG.5B

```
TCT TTG CCA ATA GTT TCA TCT TCC GAG GCC AAT AAA GTG CTC ACG AGA   1205
Ser Leu Pro Ile Val Ser Ser Ser Glu Ala Asn Lys Val Leu Thr Arg
        380             385             390

GCG CCC ATC TTA CAA TCA ACA CCT GTC ACA CCC CCA CCA CTC CCG CCA   1253
Ala Pro Ile Leu Gln Ser Thr Pro Val Thr Pro Pro Pro Leu Pro Pro
        395             400             405

GCC TTT GGA GGC ACC AGT AAA ATA GAC CAG TAT TCT CGA ATT CTC TTC   1301
Ala Phe Gly Gly Thr Ser Lys Ile Asp Gln Tyr Ser Arg Ile Leu Phe
410             415             420             425

CCA GTT GCA TTT GCA GGA TTC AAC CTT GTG TAC TGG GTA GTT TAT CTT   1349
Pro Val Ala Phe Ala Gly Phe Asn Leu Val Tyr Trp Val Val Tyr Leu
                430             435             440

TCC AAA GAT ACA ATG GAA GTG AGT AGC AGT GTT GAA TAGCTTTTCC AGGACAA 1402
Ser Lys Asp Thr Met Glu Val Ser Ser Ser Val Glu
            445             450
```

FIG.5C

```
GAATTCCGCG CGGGGAAGGG AAGAAGAGGA CGAGGTGGCG CAGAGACCGC GGGAGAACAC      60
AGTGCCTCCG GAGGAAATCT GCTCGGTCCC CGGCAGCCGC GCTTCCCCTT TGATGTTTTG     120
GTACGCCGTG GCCATGCGCC TCACATTAGA ATTACTGCAC TGGGCAGACT AAGTTGGATC     180

TCCTCTCTTC AGTGAAACCC TCAATTCCAT CAAAAACTAA AGGG ATG TGG AGA GTG      236
                                                 Met Trp Arg Val
                                                  1
```

| CGG | AAA | AGG | GGC | TAC | TTT | GGG | ATT | TGG | TCC | TTC | CCC | TTA | ATA | ATC | GCC | 284 |
|---|---|---|---|---|---|---|---|---|---|---|---|---|---|---|---|---|
| Arg | Lys | Arg | Gly | Tyr | Phe | Gly | Ile | Trp | Ser | Phe | Pro | Leu | Ile | Ile | Ala | |
| 5 | | | | 10 | | | | | 15 | | | | | | 20 | |

| GCT | GTC | TGT | GCG | CAG | AGT | GTC | AAT | GAC | CCT | AGT | AAT | ATG | TCG | CTG | GTT | 332 |
|---|---|---|---|---|---|---|---|---|---|---|---|---|---|---|---|---|
| Ala | Val | Cys | Ala | Gln | Ser | Val | Asn | Asp | Pro | Ser | Asn | Met | Ser | Leu | Val | |
| | | | | 25 | | | | | 30 | | | | | 35 | | |

| AAA | GAG | ACG | GTG | GAT | AGA | CTC | CTG | AAA | GGC | TAT | GAC | ATT | CGT | CTG | AGA | 380 |
|---|---|---|---|---|---|---|---|---|---|---|---|---|---|---|---|---|
| Lys | Glu | Thr | Val | Asp | Arg | Leu | Leu | Lys | Gly | Tyr | Asp | Ile | Arg | Leu | Arg | |
| | | | 40 | | | | | 45 | | | | | 50 | | | |

| CCA | GAT | TTT | GGA | GGT | CCC | CCC | GTG | GCT | GTG | GGG | ATG | AAC | ATT | GAC | ATT | 428 |
|---|---|---|---|---|---|---|---|---|---|---|---|---|---|---|---|---|
| Pro | Asp | Phe | Gly | Gly | Pro | Pro | Val | Ala | Val | Gly | Met | Asn | Ile | Asp | Ile | |
| | | 55 | | | | | 60 | | | | | 65 | | | | |

| GCC | AGC | ATC | GAT | ATG | GTT | TCT | GAA | GTC | AAT | ATG | GAT | TAT | ACC | TTG | ACA | 476 |
|---|---|---|---|---|---|---|---|---|---|---|---|---|---|---|---|---|
| Ala | Ser | Ile | Asp | Met | Val | Ser | Glu | Val | Asn | Met | Asp | Tyr | Thr | Leu | Thr | |
| 70 | | | | | 75 | | | | | | 80 | | | | | |

| ATG | TAC | TTT | CAA | CAA | GCC | TGG | AGA | GAT | AAG | ACG | CTG | TCC | TAT | AAT | GTA | 524 |
|---|---|---|---|---|---|---|---|---|---|---|---|---|---|---|---|---|
| Met | Tyr | Phe | Gln | Gln | Ala | Trp | Arg | Asp | Lys | Arg | Leu | Ser | Tyr | Asn | Val | |
| 85 | | | | | 90 | | | | | 95 | | | | | 100 | |

| ATA | CCT | TTA | AAC | TTG | ACT | CTG | GAC | AAC | AGA | GTG | GCA | GAC | CAG | CTC | TGG | 572 |
|---|---|---|---|---|---|---|---|---|---|---|---|---|---|---|---|---|
| Ile | Pro | Leu | Asn | Leu | Thr | Leu | Asp | Asn | Arg | Val | Ala | Asp | Gln | Leu | Trp | |
| | | | | 105 | | | | | 110 | | | | | 115 | | |

| GTG | CCT | GAT | ACC | TAT | TTC | CTG | AAC | GAT | AAG | AAG | TCA | TTT | GTG | CAC | GGA | 620 |
|---|---|---|---|---|---|---|---|---|---|---|---|---|---|---|---|---|
| Val | Pro | Asp | Thr | Tyr | Phe | Leu | Asn | Asp | Lys | Lys | Ser | Phe | Val | His | Gly | |
| | | | 120 | | | | | 125 | | | | | 130 | | | |

| GTG | ACT | GTT | AAG | AAC | CGC | ATG | ATT | CGC | CTG | CAT | CCT | GAT | GGC | ACC | GTC | 668 |
|---|---|---|---|---|---|---|---|---|---|---|---|---|---|---|---|---|
| Val | Thr | Val | Lys | Asn | Arg | Met | Ile | Arg | Leu | His | Pro | Asp | Gly | Thr | Val | |
| | | 135 | | | | | 140 | | | | | 145 | | | | |

| CTT | TAT | GGA | CTC | AGA | ATC | ACA | ACC | ACA | GCT | GCC | TGC | ATG | ATG | GAC | CTA | 716 |
|---|---|---|---|---|---|---|---|---|---|---|---|---|---|---|---|---|
| Leu | Tyr | Gly | Leu | Arg | Ile | Thr | Thr | Thr | Ala | Ala | Cys | Met | Met | Asp | Leu | |
| | | 150 | | | | 155 | | | | | 160 | | | | | |

FIG.6A

| | | | | | | | | | | | | | | | | |
|---|---|---|---|---|---|---|---|---|---|---|---|---|---|---|---|---|
| AGG | AGG | TAC | CCA | CTG | GAT | GAA | CAA | AAC | TGC | ACC | TTG | GAA | ATT | GAG | AGC | 764 |
| Arg 165 | Arg | Tyr | Pro | Leu | Asp 170 | Glu | Gln | Asn | Cys 175 | Thr | Leu | Glu | Ile | Glu 180 | Ser | |
| TAT | GGA | TAC | ACA | ACT | GAT | GAC | ATT | GAG | TTT | TAC | TGG | CGT | GGC | GAT | GAT | 812 |
| Tyr | Gly | Tyr | Thr | Thr 185 | Asp | Asp | Ile | Glu | Phe 190 | Tyr | Trp | Arg | Gly | Asp 195 | Asp | |
| AAT | GCA | GTA | ACA | GGA | GTA | ACG | AAA | ATT | GAA | CTT | CCA | CAG | TTC | TCT | ATT | 860 |
| Asn | Ala | Val | Thr 200 | Gly | Val | Thr | Lys | Ile 205 | Glu | Leu | Pro | Gln | Phe 210 | Ser | Ile | |
| GTA | GAT | TAC | AAA | CTT | ATC | ACC | AAG | AAG | GTT | GTT | TTT | TCC | ACA | GGT | TCC | 908 |
| Val | Asp | Tyr 215 | Lys | Leu | Ile | Thr | Lys 220 | Lys | Val | Val | Phe | Ser 225 | Thr | Gly | Ser | |
| TAT | CCC | AGG | TTA | TCC | CTC | AGC | TTT | AAG | CTT | AAG | AGA | AAC | ATT | GGC | TAC | 956 |
| Tyr | Pro 230 | Arg | Leu | Ser | Leu | Ser 235 | Phe | Lys | Leu | Lys | Arg 240 | Asn | Ile | Gly | Tyr | |
| TTT | ATC | CTG | CAA | ACA | TAC | ATG | CCT | TCC | ATC | CTG | ATT | ACC | ATC | CTC | TCC | 1004 |
| Phe 245 | Ile | Leu | Gln | Thr | Tyr 250 | Met | Pro | Ser | Ile | Leu 255 | Ile | Thr | Ile | Leu | Ser 260 | |
| TGG | GTC | TCC | TTC | TGG | ATT | AAT | TAC | GAT | GCT | TCA | GCT | GCA | AGG | GTG | GCA | 1052 |
| Trp | Val | Ser | Phe | Trp 265 | Ile | Asn | Tyr | Asp | Ala 270 | Ser | Ala | Ala | Arg | Val 275 | Ala | |
| TTA | GGA | ATC | ACA | ACT | GTC | CTC | ACA | ATG | ACC | ACA | ATC | AAC | ACC | CAC | CTC | 1100 |
| Leu | Gly | Ile | Thr | Thr 280 | Val | Leu | Thr | Met 285 | Thr | Thr | Ile | Asn | Thr 290 | His | Leu | |
| CGG | GAA | ACT | CTC | CCT | AAA | ATC | CCC | TAT | GTG | AAG | GCC | ATT | GAC | ATG | TAC | 1148 |
| Arg | Glu | Thr 295 | Leu | Pro | Lys | Ile | Pro 300 | Tyr | Val | Lys | Ala | Ile 305 | Asp | Met | Tyr | |
| CTG | ATG | GGG | TGC | TTT | GTC | TTC | GTT | TTC | ATG | GCC | CTT | CTG | GAA | TAT | GCC | 1196 |
| Leu | Met 310 | Gly | Cys | Phe | Val | Phe 315 | Val | Phe | Met | Ala | Leu 320 | Leu | Glu | Tyr | Ala | |
| CTA | GTC | AAC | TAC | ATC | TTC | TTT | GGG | AGG | GGG | CCC | CAA | CGC | CAA | AAG | AAA | 1244 |
| Leu 325 | Val | Asn | Tyr | Ile | Phe 330 | Phe | Gly | Arg | Gly | Pro 335 | Gln | Arg | Gln | Lys | Lys 340 | |
| GCA | GCT | GAG | AAG | GCT | GCC | AGT | GCC | AAC | AAT | GAG | AAG | ATG | CGC | CTG | GAT | 1292 |
| Ala | Ala | Glu | Lys | Ala 345 | Ala | Ser | Ala | Asn | Asn 350 | Glu | Lys | Met | Arg | Leu 355 | Asp | |

FIG.6B

| | | | | | | | | | | | | | | | |
|---|---|---|---|---|---|---|---|---|---|---|---|---|---|---|---|
| GTC | AAC | AAG | ATG | GAC | CCC | CAT | GAG | AAC | ATC | TTA | CTG | AGC | ACT | CTC | GAG |
| Val | Asn | Lys | Met | Asp | Pro | His | Glu | Asn | Ile | Leu | Leu | Ser | Thr | Leu | Glu |
| | | | 360 | | | | | 365 | | | | | 370 | | |

1340

ATA AAA AAT GAA ATG GCC ACA TCT GAG GCT GTG ATG GGA CTT GGA GAC   1388
Ile Lys Asn Glu Met Ala Thr Ser Glu Ala Val Met Gly Leu Gly Asp
        375             380                 385

CCC AGA AGC ACA ATG CTA GCC TAT GAT GCC TCC AGC ATC CAG TAT CGG   1436
Pro Arg Ser Thr Met Leu Ala Tyr Asp Ala Ser Ser Ile Gln Tyr Arg
    390             395                 400

AAA GCT GGG TTG CCC AGG CAT AGT TTT GGC CGA AAT GCT CTG GAA CGA   1484
Lys Ala Gly Leu Pro Arg His Ser Phe Gly Arg Asn Ala Leu Glu Arg
405             410                 415                 420

CAT GTG GCG CAA AAG AAA AGT CGC CTG AGG AGA CGC GCC TCC CAA CTG   1532
His Val Ala Gln Lys Lys Ser Arg Leu Arg Arg Arg Ala Ser Gln Leu
                425                 430                 435

AAA ATC ACC ATC CCT GAC TTG ACT GAT GTG AAT GCC ATA GAT CGG TGG   1580
Lys Ile Thr Ile Pro Asp Leu Thr Asp Val Asn Ala Ile Asp Arg Trp
        440                 445                 450

TCC CGC ATA TTC TTC CCA GTG GTT TTT TCC TTC TTC AAC ATC GTC TAT   1628
Ser Arg Ile Phe Phe Pro Val Val Phe Ser Phe Phe Asn Ile Val Tyr
        455             460                 465

TGG CTT TAT TAT GTG AAC  —>   TAAAACATGG CCTCCCACTG GAAGCAAGGA CTAGATTCC   1685
Trp Leu Tyr Tyr Val Asn
470

TCCTCAAACC AGTTGTACAG CCTGATGTAG GACTTGGAAA ACACATCAAT CCAGGACAAA   1745
AGTGACGCTA AAATACCTTA GTTGCTGGCC TATCCTGTGG TCCATTTCAT ACCATTTGGG   1805
TTGCTTCTGC TAAGTAATGA ATACACTAAG GTCCTTGTGG TTTTCCAGTT AAAACGCAAG   1865
T                                                                  1866

FIG.6C

STABLY HUMAN TRANSFECTED RODENT FIBROBLAST CELL LINE EXPRESSING HUMAN GABA-A RECEPOTORS, AND CLONED HUMAN GABA-A RECEPTOR SUBUNIT CDNA SEQUENCES

This is a continuation-in-part of U.S. application Ser. No. 07/971,767, filed Feb. 2, 1993 now abandoned.

This invention concerns a cell line, and in particular relates to a stable cell line capable of expressing human or animal $GABA_A$ receptors. The invention further concerns the cloning of novel cDNA sequences encoding particular subunits of the human $GABA_A$ receptor. In addition, the invention relates to the use of the cell line in a screening technique for the design and development of subtype-specific medicaments.

Gamma-amino butyric acid (GABA) is a major inhibitory neurotransmitter in the central nervous system. It mediates fast synaptic inhibition by opening the chloride channel intrinsic to the $GABA_A$ receptor. This receptor comprises a multimeric protein of molecular size 230–270 kDa with specific binding sites for a variety of drugs including benzodiazepines, barbiturates and $\beta$-carbolines, in addition to sites for the agonist ligand GABA (for reviews see Stephenson, *Biochem. J.*, 1988, 249, 21; Olsen and Tobin, *Faseb J.*, 1990, 4, 1469; and Sieghart, *Trends in Pharmacol. Sci.*, 1989, 10, 407).

Molecular biological studies demonstrate that the receptor is composed of several distinct types of subunit, which are divided into four classes ($\alpha$, $\beta$, $\gamma$, and $\delta$) based on their sequence similarities. To date, six types of $\alpha$ (Schofield et al., *Nature (London)*, 1987, 328, 221; Levitan et al., *Nature (London)*, 1988, 335, 76; Ymer et al., *EMBO J.*, 1989, 8, 1665; Pritchett & Seeberg, *J. Neurochem.*, 1990, 54, 802; Luddens et al., *Nature (London)*, 1990, 346, 648; and Khrestchatisky et al., *Neuron*, 1989, 3, 745), three types of $\beta$ (Ymer et al., *EMBO J.*, 1989, 8, 1665), two types of $\gamma$ (Ymer et al., *EMBO J.*, 1990, 9, 3261; and Shivers et al., *Neuron*, 1989, 3, 327) and one $\delta$ subunit (Shivers et al., *Neuron*, 1989, 3, 327) have been identified.

The differential distribution of many of the subunits has been characterised by in situ hybridisation (Sequier et al., *Proc. Natl. Acad. Sci. USA*, 1988, 85, 7815; Malherbe et al., *J. Neurosci.*, 1990, 10, 2330; and Shivers et al., *Neuron*, 1989, 3, 327) and this has permitted it to be speculated which subunits, by their co-localisation, could theoretically exist in the same receptor complex.

Various combinations of subunits have been co-transfected into cells to identify synthetic combinations of subunits whose pharmacology parallels that of bona fide $GABA_A$ receptors in vivo (Pritchett et al., *Science*, 1989, 245, 1389; Malherbe et al., *J. Neurosci.*, 1990, 10, 2330; Pritchett and Seeberg, *J. Neurochem.*, 1990, 54, 1802; and Luddens et al., *Nature (London)*, 1990, 346, 648). This approach has revealed that, in addition to an $\alpha$ and $\beta$ subunit, either $\gamma_1$ or $\gamma_2$ (Pritchett et al., *Nature (London)*., 1989, 338, 582; Ymer et al., *EMBO J.*, 1990, 9, 3261; and Malherbe et al., *J. Neurosci.*, 1990, 10, 2330) or $\gamma_3$ (Herb et al., *Proc. Natl. Acad. Sci. USA*, 1992, 89, 1433; Knoflach et al., *FEBS Lett.*, 1991, 293, 191; and Wilson-Shaw et al., *FEBS Lett.*, 1991, 284, 211) is also generally required to confer benzodiazepine sensitivity, and that the benzodiazepine pharmacology of the expressed receptor is largely dependent on the identity of the $\alpha$ and $\gamma$ subunits present. Receptors containing a $\delta$ subunit (i.e. $\alpha\beta\delta$) do not appear to bind benzodiazepines (Shivers et al., *Neuron*, 1989, 3, 327). Combinations of subunits have been identified which exhibit the pharmacological profile of a $BZ_1$ type receptor ($\alpha_1\beta_1\gamma_2$) and a $BZ_2$ type receptor ($\alpha_2\beta_1\gamma_2$ or $\alpha_3\beta_1\gamma_2$, Pritchett et al., *Nature (London)*, 1989, 338, 582), as well as two $GABA_A$ receptors with a novel pharmacology, $\alpha_5\beta_2\gamma_2$ (Pritchett and Seeberg, *J. Neurochem.*, 1990, 54, 1802) and $\alpha_6\beta_2\gamma_2$ (Luddens et al., *Nature (London)*, 1990, 346, 648). Although the pharmacology of these expressed receptors appears similar to that of those identified in brain tissue by radioligand binding, it has nonetheless not been shown that these receptor subunit combinations exist in vivo.

The present invention is concerned with the production of permanently transfected cells containing the $GABA_A$ receptor, which will be useful for screening for drugs which act on this receptor. The $GABA_A$ receptor has previously been expressed in Xenopus oocytes (Sigel et al., *Neuron*, 1990, 5, 703–711) and in transiently transfected mammalian cells (Pritchett et al., *Science*, 1989, 245, 1389–1392). However, both of those systems involve transient expression and are unsuitable for screening purposes.

We have now achieved the stable expression of the receptor.

Accordingly, the present invention provides a stably co-transfected eukaryotic cell line capable of expressing a $GABA_A$ receptor, which receptor comprises at least one alpha, one beta and one gamma subunit.

This has been achieved by co-transfecting cells with three expression vectors, each harbouring cDNAs encoding for an $\alpha$, $\beta$ or $\gamma$ $GABA_A$ receptor subunit. In a further aspect, therefore, the present invention provides a process for the preparation of a eukaryotic cell line capable of expressing a $GABA_A$ receptor, which comprises stably co-transfecting a eukaryotic host cell with at least three expression vectors, one such vector harbouring the cDNA sequence encoding for an alpha, another such vector harbouring the cDNA sequence encoding for a beta, and a third such vector harbouring the cDNA sequence encoding for a gamma $GABA_A$ receptor subunit. The stable cell-line which is established expresses an $\alpha\beta\gamma$ $GABA_A$ receptor. Each receptor thereby expressed, comprising a unique combination of $\alpha$, $\beta$ and $\gamma$ subunits, will be referred to hereinafter as a $GABA_A$ receptor "subunit combination". Pharmacological and electrophysiological data confirm that the recombinant $\alpha\beta\gamma$ receptor expressed by the cells of the present invention has the properties expected of a native $GABA_A$ receptor.

Expression of the $GABA_A$ receptor may be accomplished by a variety of different promoter-expression systems in a variety of different host cells. The eukaryotic host cells suitably include yeast, insect and mammalian cells. Preferably the eukaryotic cells which can provide the host for the expression of the receptor are mammalian cells. Suitable host cells include rodent fibroblast lines, for example mouse Ltk⁻, Chinese hamster ovary (CHO) and baby hamster kidney (BHK); HeLa; and HEK293 cells. It is necessary to incorporate at least one $\alpha$, one $\beta$ and one $\gamma$ subunit into the cell line in order to produce the required receptor. Within this limitation, the choice of receptor subunit combination is made according to the type of activity or selectivity which is being screened for. For example, benzodiazepines (designated BZ) represent one class of drugs which act upon the $GABA_A$ receptor. The presence of an $\alpha_1$ subunit is specific for a class of benzodiazepines having the pharmacology designated $BZ_1$; whereas $\alpha_2$ to $\alpha_5$ define different pharmacological profiles, broadly designated as $BZ_2$. The type of $\beta$ subunit is not critical in defining the class of benzodiazepine, although a $\beta$ subunit is required. The $\gamma$ subunit is also important in defining BZ selectivity. It is likely that differentiation between $\alpha$ subunit selectivity is conferred by the identity of the particular $\gamma$ subunit present.

In order to employ this invention most effectively for screening purposes, it is preferable to build up a library of cell lines, each with a different combination of subunits. Typically a library of 5 or 6 cell line types is convenient for this purpose. Preferred subunit combinations include: $\alpha_1\beta_1\gamma_2$; $\alpha_1\beta_2\gamma_2$; $\alpha_2\beta_1\gamma_1$; $\alpha_2\beta_1\gamma_2$; $\alpha_2\beta_1\gamma_3$; $\alpha_3\beta_1\gamma_2$; $\alpha_3\beta_1\gamma_3$; $\alpha_4\beta_1\gamma_2$; $\alpha_5\beta_1\gamma_2$; and $\alpha_6\beta_1\gamma_2$; especially $\alpha_1\beta_1\gamma_{2L}$.

The DNAs for the receptor subunits can be obtained from known sources, and are generally obtained as specific nucleotide sequences harboured by a standard cloning vector such as those described, for example, by Maniatis et al. in *Molecular Cloning, A Laboratory Manual*, Cold Spring Harbor Press, New York, 2nd edition, 1989. Preferably the cDNA sequences are derived from the human gene. However, for screening purposes, cDNAs from other species are also suitable, such as bovine or rat DNA. Known sources of $GABA_A$ receptor subunit cDNAs are as follows:

$\alpha_1$ bovine} Schofield et al, *Nature*, 1987, 328, 221–227

$\beta_1$ bovine}

$\alpha_1$ human} Schofield et al, *FEBS Lett.*, 1989, 244, 361–364

$\beta_1$ human}

$\alpha_2$ rat Khrestchatisky et al, *J. Neurochem.*, 1991, 56, 1717.

$\alpha_2$ bovine} Levitan et al, *Nature*, 1988, 335, 76–79

$\alpha_3$ bovine}

$\alpha_4$ rat Wisden et al., *FEBS Lett.*, 1991, 289, 227

$\alpha_4$ bovine Ymer et al, *FEBS Lett.*, 1989, 258, 119–122

$\alpha_5$ rat Pritchett and Seeburg, *J. Neurochem.*, 1990, 54, 1802–1804.

$\alpha_6$ rat Luddens et al, *Nature*, 1990, 346, 648–651

$\alpha_6$ bovine $\beta_2$ bovine} Ymer et al, *EMBO J.*, 1989, 8, 1665–1670

$\beta_2$ rat}

$\beta_3$ bovine}

$\beta_3$ rat}

$\gamma_1$ human} Ymer et al, *EMBO J.*, 1990, 9, 3261–3267

$\gamma_1$ rat}

$\gamma_1$ bovine}

$\gamma_2$ human Pritchett et al., *Nature*, 1989, 338, 582–585

$\gamma_2$ bovine Whiting et al, *Proc. Natl. Acad. Sci. USA*, 1990, 57, 9966–9970. $\gamma_3$ rat Herb et al, *Proc. Natl. Acad. Sci. USA*, 1992, 89, 1433; and Knoflach et al., *FEBS Lett.*, 1991, 293, 191

$\gamma_3$ mouse Wilson-Shaw et al, *FEBS Lett.*, 1991, 284, 211

$\delta$ rat Shivers et al, *Neuron*, 1989, 3, 327

Certain cDNA sequences encoding various subunits of the human $GABA_A$ receptor have hitherto been unavailable. These include in particular the sequences encoding the $\alpha_2$, $\alpha_3$, $\alpha_5$, $\alpha_6$ and $\beta_2$ subunits, which nucleotide sequences are accordingly novel. We have now ascertained the cDNA sequences of the $\alpha_2$, $\alpha_3$, $\alpha_5$, $\alpha_6$ and $\beta_2$ subunits of the human $GABA_A$ receptor. These nucleotide sequences, together with the deduced amino acid sequences corresponding thereto, are depicted in FIGS. 2A–C, 3A–C, 4A–C, 5A–B and 6A–C of the accompanying drawings. The present invention accordingly provides in several additional aspects DNA molecules encoding the $\alpha_2$, $\alpha_3$, $\alpha_5$, $\alpha_6$ and $\beta_2$ subunits of the human $GABA_A$ receptor comprising all or a portion of the sequences depicted in FIGS. 2A–C, 3A–C, 4A–C, 5A–B and 6A–C respectively, or substantially similar sequences.

The sequencing of the novel cDNA molecules in accordance with the invention can conveniently be carried out by the standard procedure described in accompanying Example 3; or may be accomplished by alternative molecular cloning techniques which are well known in the art, such as those described by Maniatis et al. in *Molecular Cloning, A Laboratory Manual*, Cold Spring Harbor Press, New York, 2nd edition, 1989.

In another aspect, the invention provides a recombinant expression vector comprising the nucleotide sequence of a $GABA_A$ receptor subunit together with additional sequences capable of directing the synthesis of the said $GABA_A$ receptor subunit in cultures of stably co-transfected eukaryotic cells.

The term "expression vectors" as used herein refers to DNA sequences that are required for the transcription of cloned copies of recombinant DNA sequences or genes and the translation of their mRNAs in an appropriate host. Such vectors can be used to express eukaryotic genes in a variety of hosts such as bacteria, blue-green algae, yeast cells, insect cells, plant cells and animal cells. Specifically designed vectors allow the shuttling of DNA between bacteria-yeast, bacteria-plant or bacteria-animal cells. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The term "cloning vector" as used herein refers to a DNA molecule, usually a small plasmid or bacteriophage DNA capable of self-replication in a host organism, and used to introduce a fragment of foreign DNA into a host cell. The foreign DNA combined with the vector DNA constitutes a recombinant DNA molecule which is derived from recombinant technology. Cloning vectors may include plasmids, bacteriophages, viruses and cosmids.

The recombinant expression vector in accordance with the invention may be prepared by inserting the nucleotide sequence of the chosen $GABA_A$ subunit into a suitable precursor expression vector (hereinafter referred to as the "precursor vector") using conventional recombinant DNA methodology known from the art. The precursor vector may be obtained commercially, or constructed by standard techniques from known expression vectors. The precursor vector suitably contains a selection marker, typically an antibiotic resistance gene, such as the neomycin or ampicillin resistance gene. The precursor vector preferably contains a neomycin resistance gene, adjacent the SV40 early splicing and polyadenylation region; an ampicillin resistance gene; and an origin of replication, e.g. pBR322 ori. The vector also preferably contains an inducible promoter, such as MMTV-LTR (inducible with dexamethasone) or metallothionin (inducible with zinc), so that transcription can be controlled in the cell line of this invention. This reduces or avoids any problem of toxicity in the cells because of the chloride channel intrinsic to the $GABA_A$ receptor.

One suitable precursor vector is pMAMneo, available from Clontech Laboratories Inc. (Lee et al., *Nature*, 1981, 294, 228; and Sardet et al., *Cell*, 1989, 56, 271). Alternatively the precursor vector pMSGneo can be constructed from the vectors pMSG and pSV2neo as described in Example 1 herein.

The recombinant expression vector of the present invention is then produced by cloning the $GABA_A$ receptor subunit cDNA into the above precursor vector. The required receptor subunit cDNA is subcloned from the vector in which it is harboured, and ligated into a restriction enzyme site, e.g. the HindIII site, in the polylinker of the precursor vector, for example pMAMneo or pMSGneo, by standard cloning methodology known from the art, and in particular by techniques analogous to those described in Example 1, step (b) herein. Before this subcloning, it is often advantageous, in order to improve expression, to modify the end of a subunit cDNA with additional 5' untranslated sequences, for example by modifying the 5' end of the $\gamma_{2L}$ subunit DNA by addition of 5' untranslated region sequences from the $\alpha_1$ subunit DNA.

One suitable expression vector of the present invention is illustrated in FIG. 1 of the accompanying drawings, in which R represents the nucleotide sequence of a given alpha, beta or gamma subunit of the $GABA_A$ receptor, and the remainder of the expression vector depicted therein is derived from the precursor vector pMSGneo and constructed as described in accompanying Example 1, steps (a) and (b).

For each cell line of the present invention, three such vectors will be necessary, one containing an $\alpha$ subunit, one containing a $\beta$ subunit, and the third containing a $\gamma$ subunit.

Cells are then co-transfected with the desired combination of three expression vectors. There are several commonly used techniques for transfection of eukaryotic cells in vitro. Calcium phosphate precipitation of DNA is most commonly used (Bachetti et al., *Proc. Natl. Acad. Sci. USA*, 1977, 74, 1590–1594; Maitland et al., *Cell*, 1977, 14, 133–141), and represents a favoured technique in the context of the present invention.

A small percentage of the host cells takes up the recombinant DNA. In a small percentage of those, the DNA will integrate into the host cell chromosome. Because the neomycin resistance gene will have been incorporated into these host cells, they can be selected by isolating the individual clones which will grow in the presence of neomycin. Each such clone is then tested to identify those which will produce the receptor. This is achieved by inducing the production, for example with dexamethasone, and then detecting the presence of receptor by means of radioligand binding.

In a further aspect, the present invention provides protein preparations of $GABA_A$ receptor subunit combinations, especially human $GABA_A$ receptor subunit combinations, derived from cultures of stably transfected eukaryotic cells. The invention also provides preparations of membranes containing subunit combinations of the $GABA_A$ receptor, especially human $GABA_A$ receptor subunit combinations, derived from cultures of stably transfected eukaryotic cells. In particular, the protein preparation and membrane preparations according to the invention will suitably contain the $\alpha_1\beta_1\gamma_2$ subunit combinations of the human $GABA_A$ receptor, and will preferably contain a human $GABA_A$ receptor consisting of the $\alpha_1\beta_1\gamma_{2L}$ subunit combinations. In an especially preferred embodiment, the invention provides cell membranes containing a human $GABA_A$ receptor consisting of the $\alpha_1\beta_1\gamma_{2L}$ subunit combinations isolated from stably transfected mouse Ltk$^-$ fibroblast cells.

The cell line, and the membrane preparations therefrom, according to the present invention have utility in screening and design of drugs which act upon the $GABA_A$ receptor, for example benzodiazepines, barbiturates, $\beta$-carbolines and neurosteroids. The present invention accordingly provides the use of the cell line described above, and membrane preparations derived therefrom, in screening for and designing medicaments which act upon the $GABA_A$ receptor. Of particular interest in this context are molecules capable of interacting selectively with $GABA_A$ receptors made up of varying subunit combinations.

It is possible to estimate a minimum level of receptor expression required for utility of the transfected cell line as a tool for radioligand binding studies and, more particularly, for drug screening. The average specific radioactivity for a tritiated receptor ligand such as [$_3$H]Ro15-1788 (see Example 2a, below) is 50–80 Ci/mmol (110–176 dpm/fmol). The amount of membrane protein used for each assay point is generally 100 μg. The absolute minimum number of specific disintegrations per minute (dpm) required to give an adequate signal to noise in a binding assay where saturation curves and $IC_{50}$ values need to be generated is about 500 dpm. 500 dpm is 2.8–4.5 fmols/100 μg which is 28–45 fmol/mg of protein. Thus, the absolute minimum level of receptor expression required is between 28 and 45 fmols/mg of protein. It will be appreciated however that at this level the cell line would probably be too inefficient for use in a drug screening programme. A more practicable minimum would be at least 100 fmols/mg of protein.

As will be readily apparent, the cell line in accordance with the present invention, and the membrane preparations derived therefrom, provide ideal systems for the study of structure, pharmacology and function of the various $GABA_A$ receptor subtypes.

BRIEF DESCRIPTION OF THE DRAWINGS

FIG. 2 panels 2A, 2B, 2C and 2D show the nucleotide sequence of the cDNA encoding the $GABA_A$ receptor $\alpha_2$ subunit (SEQ ID NO:11) together with the deduced amino acid sequence (SEQ ID NO:12) corresponding thereto.

FIG. 3 panels 3A, 3B and 3C show the nucleotide sequence of the cDNA encoding the $GABA_A$ receptor $\alpha_3$ subunit (SEQ ID NO:13) together with the deduced amino acid sequence (SEQ ID NO:14) corresponding thereto.

FIG. 4 panels 4A, 4B and 4C show the nucleotide sequence of the cDNA encoding the $GABA_A$ receptor $\alpha_5$ subunit (SEQ ID NO:15) together with the deduced amino acid sequence (SEQ ID NO:16) corresponding thereto.

FIG. 5 panels 5A, 5B and 5C show the nucleotide sequence of the cDNA encoding the $GABA_A$ receptor $\alpha_6$ subunit (SEQ ID NO:17) together with the deduced amino acid sequence (SEQ ID NO:18) corresponding thereto.

FIG. 6 panels 6A, 6B and 6C show the nucleotide sequence of the cDNA encoding the $GABA_A$ receptor $\beta_2$ subunit (SEQ ID NO:19) together with the deduced amino acid sequence (SEQ ID NO:20) corresponding thereto.

Figure 1:
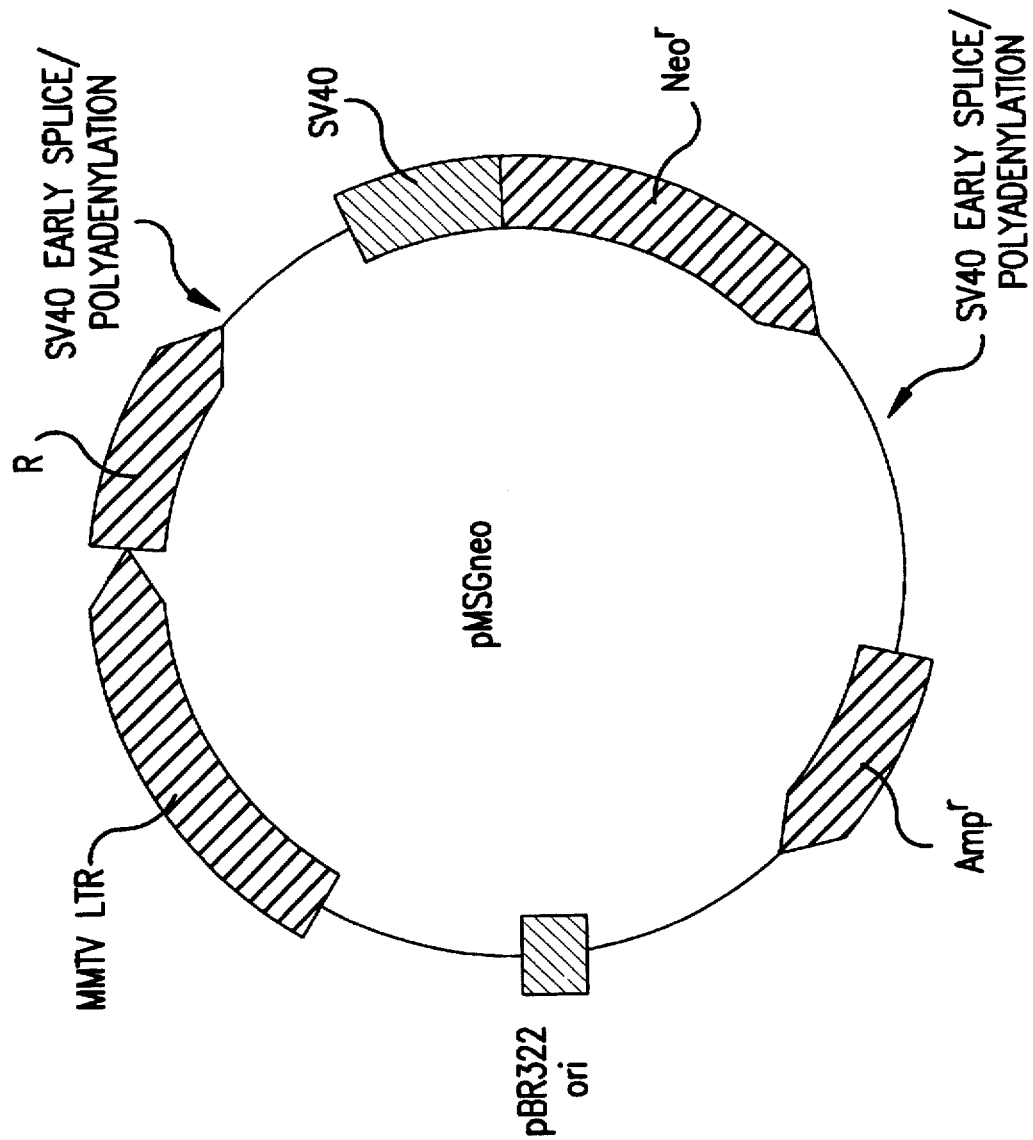
FIG. 1 represents the expression vector pMSGneo.

The following non-limiting Examples illustrate the present invention.

EXAMPLE 1

Preparation of $\alpha_1\beta_1\gamma_{2L}$ Transfected Cells a) Construction of eukaryotic expression vector pMSG-neo The approx. 2500 base pair HindIII-EcoRI fragment of the vector pMSG (purchased from Pharmacia Biosystems Limited, Milton Keynes, United Kingdom), containing the gpt structural gene and SV40 polyadenylation signals was replaced by the approx. 2800 base pair HindIII-EcoRI fragment of pSV2neo (Southern, P. J. and Berg, P. J., *Molecular and Applied Genetics*, 1, 327–341, 1982) containing the neomycin resistance gene Neo$^r$ and SV40 polyadenylation signals. The EcoRI and HindIII sites were then removed by restriction digesting, blunt ending with klenow polymerase, and religating. EcoRI and HindIII cloning sites were then inserted at the XhoI and SmaI sites of the polylinker by conventional techniques using EcoRI and HindIII linkers.

b) Cloning of subunit cDNAs into pMSGneo

Bovine $\alpha_1$ and $\beta_1$ GABA$_A$ receptor cDNAs were obtained from the Molecular Neurobiology Unit, MRC Centre, Hills Road, Cambridge (Scholfield, P. et al. *Nature*, 328, 221–227, 1987). Bovine $\gamma_2$ cDNA was cloned by the method of Whiting, P. et al. (*Proc. Natl. Acad. Sci. USA*, 87, 9966–9970, 1990). Bovine $\alpha_1$ was subcloned from pbGRαsense by digestion with EcoRI, blunt ending the DNA with klenow polymerase, addition of HindIII linkers by ligation, digestion with HindIII and ligation into the HindIII site of pMSGneo. Bovine $\beta_1$ was subcloned from pbGRαsense by restriction digestion with EcoRI (partial digestion), klenow polymerase blunt ending, ligation of HindIII linkers, restriction digestion with HindIII and ligation into HindIII site of pMSGneo. Before subcloning into pMSGneo, the bovine $\gamma_2$ cDNA was modified from the published sequence as follows. The 5' untranslated region of the bovine $\alpha_1$ cDNA (bases 60–200 of the published sequence) was added to the 5' end of the published $\gamma_2$ sequence by amplifying the $\alpha_1$ untranslated region using polymerase chain reaction, and then subcloning the product into the 5' BamHI (site in the polylinker of the Bluescript Sk⁻ cloning vector; Bluescript vector purchased from Stratagene, San Diego, U.S.A.) HindIII sites of the $\gamma_2$ cDNA. The modified $\gamma_2$ cDNA was then subcloned into pMSGneo by digestion with XbaI (site in the polylinker of the cloning vector), blunt ending with klenow polymerase, ligation of XhoI linkers, digestion with XhoI (site in the polylinker of the cloning vector), and ligation into XhoI site of pMSGneo.

c) Co-transfection of mouse Ltk⁻ cells

Ltk⁻ cells were obtained from the Salk Institute for Biological Studies, San Diego, Calif. Cells were grown at 37° C., 5–8% CO$_2$, in Modified Eagles Medium containing penicillin, streptomycin and 10% fetal calf serum. The expression vector harbouring the GABA$_A$ receptor subunit DNAs for co-transfection was prepared by a standard protocol (Chen, C. and Okayama, H., *BioTechniques*, 6, 632–638, 1988). For co-transfection, Ltk⁻ cells were plated in dishes (approx. 2×10$^5$ cells/dish) and grown overnight. The transfection was performed by calcium phosphate precipitation using a kit (purchased from 5 Prime→3 Prime Products, Westchester, Pa.). Co-transfection was performed according to manufacturers' instructions, using 5 µg of each subunit DNA construct per 10 cm dish of cells. After 2 days in culture the cells were divided 1:8 into culture medium containing 1 mg/ml neomycin [Geneticin (obtainable from Gibco BRL, Paisley, Scotland, U.K.)]. After a further week the concentration was increased to 1.5 mg/ml, and then 2 mg/ml 1 week after that. Resistant clones of cells were isolated and subcloned using cloning cylinders. Subclones were analysed using radioligand binding: subclones were grown in 10 cm culture dishes, and when confluent changed into culture medium containing 1 µM dexamethasone (obtainable from Sigma Chemical Company, Poole, Dorset, United Kingdom). 3–5 days later the cells were harvested, membranes prepared and used for radioligand binding (see Example 2, step (a) below) using the benzodiazepine antagonist [$_3$H]Ro15-1788 (obtained from New England Nuclear, Du Pont (U.K.) Ltd, Stevenage, United Kingdom). The clone expressing the highest amount of $^3$H Ro15-1788 binding was subcloned from a single cell by limiting dilution. The resultant clonal population of cells described below is referred to as population A.

EXAMPLE 2

Characterization of $\alpha_1\beta_1\gamma_{2L}$ Transfected Cells a) Radioligand binding The nature of the recombinant $\alpha_1\beta_1\gamma_{2L}$ GABA$_A$ receptors prepared as described in Example 1 was addressed by characterization of the benzodiazepine (BZ) binding pharmacology. The number of recombinant GABA$_A$ receptors expressed by the stably transfected cell lines is quantitated by the binding of the radioligand [$_3$H]Ro15-1788. This benzodiazepine compound binds specifically to the benzodiazepine site of GABA$_A$ receptors constituted by an $\alpha$, $\beta$ and a $\gamma_2$ subunit. It is thought that there is one benzodiazepine binding site per receptor molecule. A [$_3$H]Ro15-1788 binding assay is performed as described below. Briefly, membranes are prepared from transfected cells, incubated with the radioligand, rapidly washed to remove unbound radioligand and quantitated by measuring the amount of radioligand specifically bound to the receptor by scintillation counting. The number of fmols [$_3$H]Ro15-1788 bound is a direct measure of the number of GABA$_A$ receptors, which can be quantitated in terms of fmols/mg of membrane protein, fmols/tissue culture dish or fmols/cell.

The [$_3$H]Ro15-1788 radioligand binding assay was performed as follows: cells which had been induced by culture in dexamethasone containing medium for 3–5 days were scraped off into 50 mM Tris, pH7.5, 100 mM NaCl in the form of Tris buffered saline (TBS) and pelleted (20,000 rpm, Sorvall RC5C centrifuge). The cell pellet was resuspended in 50 mM Tris, pH7.5, homogenised using an Ultra-Turrax homogeniser and then pelleted as above. This was repeated once more, and the cells then resuspended in TBS (0.4 ml per original 10cm dish of cells). Radioligand binding was performed in 0.1 ml final volume TBS, containing 5–15 fmols of [$_3$H]Ro15-1788 binding sites. After 1 hour incubation on ice the membranes were harvested onto filters using a Brandel cell harvester, washed with cold TBS, and bound radioactivity determined by scintillation counting. The recombinant $\alpha_1\beta_1\gamma_{2L}$ receptors bound [$_3$H]Ro15-1788 with high affinity (K$_D$ 0.4 nM), at levels of up to 200 fmols/10 cm dish of cells. The recombinant $\alpha_1\beta_1\gamma_{2L}$ GABA$_A$ cell line described in Example 1 expressed around 650 fmols/mg of protein. No binding was seen to either untransfected Ltk⁻ cells, or population A cells which had not been induced by addition of dexamethasone to the culture medium, confirming that the [$_3$H]Ro15-1788 was binding to recombinant $\alpha_1\beta_1\gamma_{2L}$ GABA$_A$ receptors. The [$_3$H]Ro15-1788 binding was inhibited by flunitrazepam, CL218872, FG8205, βCCM, zolpidem and Ro15-4513, confirming the BZ pharmacology of the recombinant receptor. Since it is established that only GABA$_A$ receptors containing an $\alpha$, a $\beta$ and a $\gamma$ subunit exhibit BZ binding (Pritchett, D. et al., *Nature*, 338, 582–585, 1989) these data confirm the nature of the recombinant $\alpha_1\beta_1\gamma_{2L}$ GABA$_A$ receptors expressed by population A cells.

b) Electrophysiology

The nature of the GABA$_A$ receptor expressed by population A cells has been extensively characterised by electrophysiological techniques, using whole cell patch clamp. When GABA is applied to the cells it binds to its specific agonist recognition site on the receptor. This results in the rapid, transient opening of the ion channel which is intrinsic to the GABA$_A$ receptor macromolecule. The ion channel is selective for chloride ions, which flow into the cell down a concentration gradient, leading to a change in the potential difference across the cell membrane. By artificially maintaining the potential difference, it is possible to measure the actual flow into the cell. When a high concentration of GABA is applied to the cell it will activate, statistically, all of the receptors on the cell. Thus the total current measured is proportional to the number of activated receptors. If certain biophysical properties of the $GABA_A$ receptors are known, it is possible to determine a crude estimate of the number of receptors per cell. The whole cell currents detected in the $GABA_A$ receptor expressing cell lines such as the recombinant $\alpha_1\beta_1\gamma_{2L}$ $GABA_A$ receptor expressing cell line described in Example 1 are up to 14 nA which is considered to be very large. This would extrapolate to tens of thousands of receptors per cell. Only cells induced by culture in the presence of dexamethasone showed responses to GABA. Concentration response curves to GABA gave a log $EC_{50}$ of 5.2, and a Hill coefficient of 1.9. The response to GABA was potentiated by BZs flunitrazepam and CL218872, by the barbiturate pentobarbitone, and by the steroid alphaxalone. The response to GABA was antagonised by both bicuculline and picrotoxin. All these electrophysiological data confirm that the recombinant $GABA_A$ receptor expressed by population A cells has all of the properties expected of a bona fide $GABA_A$ receptor.

EXAMPLE 3

Isolation and Sequencing of CDNAs Encoding Human $GAGA_A$ Receptor $\alpha_2$, $\alpha_3$, $\alpha_5$, $\alpha_6$ & $\beta_2$ Subunits a) cDNA libraries cDNAs were cloned from human foetal brain ($\alpha_2$, $\alpha_3$), hippocampal ($\alpha_5$, $\beta_2$) and cerebellum ($\alpha_6$) lambda bacteriophage cDNA libraries. All cDNA libraries were constructed in the lambdaZAP vector, and were purchased from Stratagene (San Diego, Calif.). For screening, the cDNA libraries were plated according to the manufacturer's instructions, at 40,000 pfu per 137 mm plate. Filter lifts were taken using Hybond N filters (Amersham) according to the manufacturer's instructions.

b) Isolation of cDNA encoding human $\alpha_2$ subunit

A bovine $\alpha_2$ cDNA (obtained from E. Barnard, Molecular Neurobiology, University of Cambridge, Hills Road, Cambridge; Levitan et al., Nature, 1988, 335, 76) was labelled to high specific activity (>1.10$^9$ cpm/μg) with $^{32}P$ by random priming and used as a probe. Library filters (8 replica filters) were prehybridised for 3-6 hours at 42° C. in 5x SSPE (1x SSPE is 0.18M NaCl, 0.01M Na$_3$PO$_4$ [pH7.4], 1 mM EDTA), 5x Denhardt's solution, 100 μg/ml salmon sperm DNA, 0.1% sodium dodecyl sulphate (SDS), 30% formamide. Hybridisation was performed in the same buffer for 18 hours at 42° C., including 0.5–1.10$^6$ cpm $^{32}P$-labelled probe per ml of hybridisation buffer. Filters were washed at 55° C. in 5x SSPE (2x 15 minutes) and 1x SSPE (2x 15 minutes) and exposed to Kodak XAR film for 1–3 days. Positive clones were plaque purified using standard techniques, and the Bluescript plasmid (Stratagene) "rescued" according to manufacturer's instructions. cDNA clones were sequenced on both strands by standard techniques using Sequenase II enzyme (United States Biochemicals). The nucleotide sequence of the cDNA encoding the human $GABA_A$ receptor $\alpha_2$ subunit, together with the deduced amino acid sequence corresponding thereto, is shown in FIGS. 2A–C of the accompanying drawings SEQ. ID.Nos: 11 and 12.

c) Isolation of cDNA encoding human $\alpha_3$ subunit

A bovine $\alpha_3$ cDNA (obtained from E. Barnard, Molecular Neurobiology, University of Cambridge, Hills Road, Cambridge; Levitan et al., Nature, 1988, 335, 76) was labelled to high specific activity with $^{32}P$ by random priming and used as a probe. Library filters were prehybridised for 3–6 hours at 55° C. in 5x SSPE, 5x Denhardt's solution, 0.1% SDS, 100 μg/ml salmon sperm DNA, and hybridised for 18 hours, 55° C. in the same buffer, containing 0.5–1×10$^6$ cpm/ml of $^{32}P$-labelled bovine $\alpha_3$ cDNA as probe. Filters were washed and exposed to X-ray film as described above; cDNA clones were rescued and sequenced as described above. The longest $\alpha_3$ cDNA clone was missing in approximately 100 bp of the 5' end of the coding region. This was obtained by PCR using as primers an oligonucleotide "anchor" primer derived from the T7 primer sequence of Bluescript vector (5'AGCGCGCGTAATACGACTCACTATAGGGCGAA3') SEQ. ID. No: 1 and an oligonucleotide derived from sequence near the 5' end of the truncated $\alpha_3$ cDNA, containing an internal Hpal site (5'CAGCATGAATTGTTAACCTCATTGTA3') SEQ. ID. No. 2. Oligonucleotides were synthesised on an Applied Biosystems 380B synthesiser. PCR was performed as described above, and a 300 bp PCR product obtained which was double digested with Hpal and Kpnl and subcloned into the similarly cut truncated $\alpha_3$ cDNA to yield a full length human $\alpha_3$ cDNA. The cDNA was sequenced on both strands as described above. The nucleotide sequence of the cDNA encoding the human $GABA_A$ receptor $\alpha_3$ subunit, together with the deduced amino acid sequence corresponding thereto, is shown in FIGS. 3A–C of the accompanying drawings SEQ. ID. Nos: 13 and 14.

d) Isolation of cDNA encoding human $\alpha_5$ subunit

A rat $\alpha_5$ cDNA obtained by polymerase chain reaction (PCR) was used as a probe to screen the cDNA library. For PCR, sequences of the oligonucleotide primers were taken from the published $\alpha_5$ sequences (Khrestchatisky et al., Neuron, 1989, 3, 745) and incorporated a Hind III site for subcloning purposes: 5' ATTATTCAAGCTTGCCATGGA-CAATGGAATGCTC3' (bp114–148) SEQ. ID. No: 3; 5'GGTTTCCAGCTTACTTTGGAGAGGTAGC3' (bp1507–1535) SEQ. ID. No: 4. PCR and subcloning of the PCR product into Bluescript SK-vector (Stratagene) for analysis was performed as described elsewhere (Whiting et al., Proc. Natl. Acad. Sci. USA, 1990, 87, 9966) except that rat brain cDNA was used as template. The rat $\alpha_5$ cDNA was labelled with $^{32}P$ and used to screen the human hippocampal cDNA library, and positive $\alpha_5$ clones rescued and sequenced as described for $\alpha_2$ above. The nucleotide sequence of the cDNA encoding the human $GABA_A$ receptor $\alpha_5$ subunit, together with the deduced amino acid sequence corresponding thereto, is shown in FIGS. 4A–C of the accompanying drawings SEQ. ID. Nos: 15 and 16.

e) Isolation of cDNA encoding human $\alpha_6$ subunit

A rat $\alpha_6$ cDNA obtained by PCR was used as a probe to screen the cDNA library. PCR was performed as described above for $\alpha_5$, using oligonucleotide primers derived from the published rat $\alpha_6$ sequence (Luddens et al., Nature, 1990, 346, 648) incorporating an EcoRI site for subcloning purposes: 5'GAGGAAGAATTCAGGAGGGTGACCT3' (bp48–72) SEQ. ID. No: 5; 5'GAAAATAACGAATTC-CAGTGTCCAGCTTT3' (bp1376–1404) SEQ. ID. No: 6. The rat $\alpha_6$ cDNA clone isolated by PCR was labelled with $^{32}P$ and used to screen a human cerebellum cDNA library, as described above for $\alpha_2$. Positive $\alpha_6$ clones were purified, rescued and sequenced as described above. None of the cDNAs contained a complete coding region. To obtain a full length cDNA 3 clones were joined together using convenient restriction sites. The nucleotide sequence of the cDNA encoding the human $GABA_A$ receptor $\alpha_6$ subunit, together with the deduced amino acid sequence corresponding thereto, is shown in FIGS. 5A–C of the accompanying drawings SEQ. ID. Nos: 17 and 18.

f) Isolation of cDNA encoding human β₂ subunit

Human β₂ cDNA was isolated using as a probe a short human β₂ cDNA obtained by PCR. PCR was performed as described above (except that the human cerebellum cDNA library was used as template), using oligonucleotide primers derived from the published rat β₂ sequence (Ymer et al., *EMBO J.*, 1989, 8, 1665), incorporating EcoRI sites for subcloning purposes: 5'CAAAAGAATTCAGCT-GAGAAAGCTGCTAATGC3' (bp1088–1119) SEQ. ID. No: 7; 5'TCAGGCGAATTCTCTTTTGTGCCACAT-GTCGTTC3' (bp1331–1364) SEQ. ID. No: 8. The human β₂ clone obtained by PCR was radiolabelled with ³²P and used to screen a human hippocampal cDNA library, as described above for α₂. The largest cDNA clone obtained lacked the 5' 500 bp of the coding region of the β₂ subunit. This was obtained by PCR using as primers an oligonucleotide "anchor" primer derived from the T7 primer sequence of the Bluescript vector (5'AGCGCGCGTAATACGACTCACTATAGGGCGAA3') SEQ. ID. No: 9, and an oligonucleotide derived from sequence near the 5' end of the truncated β₂ cDNA, containing a KpnI site (5'CATCCAGTGGGTACCTCCTTAGGT3') SEQ. ID. No: 10. PCR was performed as described above, and a 700 bp PCR product obtained which was digested with kpnI and subcloned into the truncated cDNA clone (also KpnI digested) to yield a full length human β₂ cDNA. The nucleotide sequence of the cDNA encoding the human GABA_A receptor β₂ subunit, together with the deduced amino acid sequence corresponding thereto, is shown in FIGS. 6A–C of the accompanying drawings SEQ. ID. Nos: 19 and 20.

We claim:

1. A stably co-transfected rodent fibroblast cell line capable of expressing a human $GABA_A$ receptor, which receptor comprises at least one alpha, at least one beta and at least one gamma subunit.

2. A stably co-transfected rodent fibroblast cell line as claimed in claim 1 which is capable of expressing human $GABA_A$ receptors at a level of at least 650 fmol/mg protein when measured using a $^3HRo15$-1788 radioligand binding assay.

3. A stably co-transfected rodent fibroblast cell line as claimed in claim 1 or claim 2 which is capable of expressing human $GABA_A$ receptors such that the cells exhibit whole cell currents of about 14 nA when measured using gamma-aminobutyric acid as the ligand in an electrophysiology assay.

4. A stably co-transfected cell line as claimed in claim 1 wherein the rodent fibroblast cell line is a mouse Ltk⁻ cell line.

5. A stably co-transfected rodent fibroblast cell line as claimed in claim 1 wherein the alpha subunit is the $\alpha_2$ subunit of the human $GABA_A$ receptor encoded by a DNA molecule comprising all or a portion of the sequence depicted in FIG. 2 herein SEQ. ID. NO.:11.

6. A stably co-transfected rodent fibroblast cell line as claimed in claim 1 wherein the alpha subunit is the $\alpha_3$ subunit of the human $GABA_A$ receptor encoded by a DNA molecule comprising all or a portion of the sequence depicted in FIG. 3 herein SEQ ID NO:13.

7. A stably co-transfected rodent fibroblast cell line as claimed in claim 1 wherein the alpha subunit is the $\alpha_5$ subunit of the human $GABA_A$ receptor encoded by a DNA molecule comprising all or a portion of the sequence depicted in FIG. 4 herein SEQ. ID. NO.:15.

8. A stably co-transfected rodent fibroblast cell line as claimed in claim 1 wherein the alpha subunit is the $\beta_6$ subunit of the human $GABA_A$ receptor encoded by a DNA molecule comprising all or a portion of the sequence depicted in FIG. 5 herein SEQ. ID. NO.:17.

9. A stably co-transfected rodent fibroblast cell line as claimed in claim 1 wherein the beta subunit is the $\beta_2$ subunit of the human $GABA_A$ receptor encoded by a DNA molecule comprising all or a portion of the sequence depicted in FIG. 6 herein SEQ. ID. NO.:19.

10. A process for the preparation of a rodent fibroblast cell line capable of expressing human $GABA_A$ receptor, which comprises stably co-transfecting a rodent fibroblast host cell with at least three expression vectors, one such vector comprising a cDNA sequence encoding a human alpha $GABA_A$ receptor subunit, another such vector comprising a cDNA sequence encoding a human beta $GABA_A$ receptor subunit, and a third such vector comprising a cDNA sequence encoding a human gamma $GABA_A$ receptor subunit.

11. A process as claimed in 10 wherein the rodent fibroblast cell line is a mouse Ltk⁻ cell line.

12. A process as claimed in claim 5 wherein the recombinant expression vectors comprise any one of said cDNA sequences in combination with additional sequences capable of directing the synthesis of said human $GABA_A$ receptor subunit.

13. A protein preparation of human $GABA_A$ receptor comprised of an alpha, a beta, and a gamma $GABA_A$ receptor subunit derived from a culture of stably co-transfected rodent fibroblast cells.

14. A membrane preparation of human GABA$_A$ receptor comprised of an alpha, a beta, and a gamma GABA$_A$ receptor subunit derived from a culture of stably co-transfected rodent fibroblast cells.

15. A protein preparation of human GABA$_A$ receptor comprised of an alpha, a beta, and a gamma GABA$_A$ receptor subunit represented by the formula $\alpha_1 B_1 \gamma_{2L}$ derived from a culture of stably co-transfected rodent fibroblast cells.

16. A membrane preparation of human GABA$_A$ receptor comprised of an alpha, a beta, and a gamma GABA$_A$ receptor subunit represented by the formula $\alpha_1 B_1 \gamma_{2L}$ derived from a culture of stably co-transfected rodent fibroblast cells.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

AGCGCGCGTA ATACGACTCA CTATAGGGCG AA        32

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CAGCATGAAT TGTTAACCTC ATTGTA        26

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ATTATTCAAG CTTGCCATGG ACAATGGAAT GCTC        34

( 2 ) INFORMATION FOR SEQ ID NO:4:

( i ) SEQUENCE CHARACTERISTICS:
        ( A ) LENGTH: 28 base pairs ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGTTTCCAGC TTACTTTGGA GAGGTAGC                28

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GAGGAAGAAT TCAGGAGGGT GACCT               25

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GAAAATAACG AATTCCAGTG TCCAGCTTT            29

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CAAAAGAATT CAGCTGAGAA AGCTGCTAAT GC         32

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TCAGGCGAAT TCTCTTTTGT GCCACATGTC GTTC       34

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGCGCGCGTA ATACGACTCA CTATAGGGCG AA 32

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CATCCAGTGG GTACCTCCTT AGGT 24

( 2 ) INFORMATION FOR SEQ ID NO:11:

( i ) SEQUENCE CHARACTERISTICS:
        ( A ) LENGTH: 2191 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Coding Sequence
        ( B ) LOCATION: 214...1566
        ( D ) OTHER INFORMATION:

( x i ) SEQUENCE DESCRIPTION: SEQ ID NO:11:

```
CCTAGCGCTC CTCTCCGGCT TCCACCAGCC CATCGCTCCA CGCTCTCTTG GCTGCTGCAG      60

TCTCGGTCTC TCTCTCTCTC TCTCTCTCTC TCTCTCTCTC TCTCTCTCTC TCTCTCTCTC     120

TCTCTCTCTC TCTCTCCCAA GTTTCCTATC TCGTCAAGAT CAGGGCAAAA GAAGAAAACA     180

CCGAATTCTG CTTGCCGTTT CAGAGCGGCG GTG ATG AAG ACA AAA TTG AAC ATC      234
                                     Met Lys Thr Lys Leu Asn Ile
                                      1               5

TAC AAC ATC GAG TTC CTG CTT TTT GTT TTC TTG GTG TGG GAC CCT GCC       282
Tyr Asn Ile Glu Phe Leu Leu Phe Val Phe Leu Val Trp Asp Pro Ala
         10                  15                  20

AGG TTG GTG CTG GCT AAC ATC CAA GAA GAT GAG GCT AAA AAT AAC ATT       330
Arg Leu Val Leu Ala Asn Ile Gln Glu Asp Glu Ala Lys Asn Asn Ile
     25                  30                  35

ACC ATC TTT ACG AGA ATT CTT GAC AGA CTT CTG GAT GGT TAC GAT AAT       378
Thr Ile Phe Thr Arg Ile Leu Asp Arg Leu Leu Asp Gly Tyr Asp Asn
 40                  45                  50                  55

CGG CTT AGA CCA GGA CTG GGA GAC AGT ATT ACT GAA GTC TTC ACT AAC       426
Arg Leu Arg Pro Gly Leu Gly Asp Ser Ile Thr Glu Val Phe Thr Asn
                 60                  65                  70

ATC TAC GTG ACC AGT TTT GGC CCT GTC TCA GAT ACA GAT ATG GAA TAT       474
Ile Tyr Val Thr Ser Phe Gly Pro Val Ser Asp Thr Asp Met Glu Tyr
             75                  80                  85

ACA ATT GAT GTT TTC TTT CGA CAA AAA TGG AAA GAT GAA CGT TTA AAA       522
Thr Ile Asp Val Phe Phe Arg Gln Lys Trp Lys Asp Glu Arg Leu Lys
         90                  95                 100

TTT AAA GGT CCT ATG AAT ATC CTT CGA CTA AAC AAT TTA ATG GCT AGC       570
Phe Lys Gly Pro Met Asn Ile Leu Arg Leu Asn Asn Leu Met Ala Ser
    105                 110                 115

AAA ATC TGG ACT CCA GAT ACC TTT TTT CAC AAT GGG AAG AAA TCA GTA       618
Lys Ile Trp Thr Pro Asp Thr Phe Phe His Asn Gly Lys Lys Ser Val
120                 125                 130                 135
```

```
GCT CAT AAT ATG ACA ATG CCA AAT AAG TTG CTT CGA ATT CAG GAT GAT       666
Ala His Asn Met Thr Met Pro Asn Lys Leu Leu Arg Ile Gln Asp Asp
            140             145                     150

GGG ACT CTG CTG TAT ACC ATG AGG CTT ACA GTT CAA GCT GAA TGC CCA       714
Gly Thr Leu Leu Tyr Thr Met Arg Leu Thr Val Gln Ala Glu Cys Pro
                155             160             165

ATG CAC TTG GAG GAT TTC CCA ATG GAT GCT CAT TCA TGT CCT CTG AAA       762
Met His Leu Glu Asp Phe Pro Met Asp Ala His Ser Cys Pro Leu Lys
        170             175             180

TTT GGC AGC TAT GCA TAT ACA ACT TCA GAG GTC ACT TAT ATT TGG ACT       810
Phe Gly Ser Tyr Ala Tyr Thr Thr Ser Glu Val Thr Tyr Ile Trp Thr
    185             190             195

TAC AAT GCA TCT GAT TCA GTA CAG GTT GCT CCT GAT GGC TCT AGG TTA       858
Tyr Asn Ala Ser Asp Ser Val Gln Val Ala Pro Asp Gly Ser Arg Leu
200             205             210                         215

AAT CAA TAT GAC CTG CTG GGC CAA TCA ATC GGA AAG GAG ACA ATT AAA       906
Asn Gln Tyr Asp Leu Leu Gly Gln Ser Ile Gly Lys Glu Thr Ile Lys
                    220             225                 230

TCC AGT ACA GGT GAA TAT ACT GTA ATG ACA GCT CAT TTC CAC CTG AAA       954
Ser Ser Thr Gly Glu Tyr Thr Val Met Thr Ala His Phe His Leu Lys
            235             240             245

AGA AAA ATT GGG TAT TTT GTG ATT CAA ACC TAT CTG CCT TGC ATC ATG      1002
Arg Lys Ile Gly Tyr Phe Val Ile Gln Thr Tyr Leu Pro Cys Ile Met
        250             255             260

ACT GTC ATT CTC TCC CAA GTT TCA TTC TGG CTT AAC AGA GAA TCT GTG      1050
Thr Val Ile Leu Ser Gln Val Ser Phe Trp Leu Asn Arg Glu Ser Val
    265             270             275

CCT GCA AGA ACT GTG TTT GGA GTA ACA ACT GTC CTA ACA ATG ACA ACT      1098
Pro Ala Arg Thr Val Phe Gly Val Thr Thr Val Leu Thr Met Thr Thr
280             285             290                         295

CTA AGC ATC AGT GCT CGG AAT TCT CTC CCC AAA GTG GCT TAT GCA ACT      1146
Leu Ser Ile Ser Ala Arg Asn Ser Leu Pro Lys Val Ala Tyr Ala Thr
                    300             305                 310

GCC ATG GAC TGG TTT ATT GCT GTT TGT TAT GCA TTT GTG TTC TCT GCC      1194
Ala Met Asp Trp Phe Ile Ala Val Cys Tyr Ala Phe Val Phe Ser Ala
            315             320             325

CTA ATT GAA TTT GCA ACT GTT AAT TAC TTC ACC AAA AGA GGA TGG ACT      1242
Leu Ile Glu Phe Ala Thr Val Asn Tyr Phe Thr Lys Arg Gly Trp Thr
        330             335             340

TGG GAT GGG AAG AGT GTA GTA AAT GAC AAG AAA AAA GAA AAG GCT TCC      1290
Trp Asp Gly Lys Ser Val Val Asn Asp Lys Lys Lys Glu Lys Ala Ser
    345             350             355

GTT ATG ATA CAG AAC AAC GCT TAT GCA GTG GCT GTT GCC AAT TAT GCC      1338
Val Met Ile Gln Asn Asn Ala Tyr Ala Val Ala Val Ala Asn Tyr Ala
360             365             370                         375

CCG AAT CTT TCA AAA GAT CCA GTT CTC TCC ACC ATC TCC AAG AGT GCA      1386
Pro Asn Leu Ser Lys Asp Pro Val Leu Ser Thr Ile Ser Lys Ser Ala
                    380             385                 390

ACC ACG CCA GAA CCC AAC AAG AAG CCA GAA AAC AAG CCA GCT GAA GCA      1434
Thr Thr Pro Glu Pro Asn Lys Lys Pro Glu Asn Lys Pro Ala Glu Ala
            395             400             405

AAG AAA ACT TTC AAC AGT GTT AGC AAA ATT GAC AGA ATG TCC AGA ATA      1482
Lys Lys Thr Phe Asn Ser Val Ser Lys Ile Asp Arg Met Ser Arg Ile
        410             415             420

GTT TTT CCA GTT TTG TTT GGT ACC TTT AAT TTA GTT TAC TGG GCT ACA      1530
Val Phe Pro Val Leu Phe Gly Thr Phe Asn Leu Val Tyr Trp Ala Thr
    425             430             435

TAT TTA AAC AGA GAA CCT GTA TTA GGG GTC AGT CCT TGAATTGAGA CCCATG    1582
Tyr Leu Asn Arg Glu Pro Val Leu Gly Val Ser Pro
440             445             450
```

```
TTATCTTTGG GATGTATAGC AACATTAAAT TTGGTTTGTT TTGCTATGTA CAGTCTGACT    1642

AATAACTGCT AATTTGTGAT CCAACATGTA CAGTATGTAT ATAGTGACAT AGCTTACCAG    1702

TAGACCTTTA ATGGAGACAT GCATTGCTA ACTCATGGAA CTGCAGACAG AAAGCACTCC     1762

ATGCGAAAAC AGCCATTGCC TTTTTAAAG ATTACCCTA GGACCTGATT TAAAGTGAAT     1822

TTCAAGTGAC CTGATTAATT TCCTATTCTT CCAAATGAGA TGAAAATGGG GATCCTGTAC    1882

AACCCTTTGT GGACCCTTTT GGTTTAGCTC TTAAGTAGGG GTATTTTCTA CTGTTGCTTA    1942

ATTATGATGG AAGATAACAT TGTCATTCCT AGATGAATCC TTTGAAGTAA CAAACATTGT    2002

ATCTGACATC AGCTCTGTTC ATGAGTGCTC AGAGTCCCTG CTAATGTAAT TGGAAGCTTG    2062

GTACACATAA GAAAAACTAG AGATTTGAAA TCTAGCTATG AATTACTCTA TATAGTATCT    2122

ATAGCCATGT ACATATTACA GCATGACAAG CTCGAAATAA TTATGAGTCA GCCCGAAAGA    2182

TGTTAATTA                                                          2191
```

( 2 ) INFORMATION FOR SEQ ID NO:12:

( i ) SEQUENCE CHARACTERISTICS:
        ( A ) LENGTH: 451 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:12:

```
Met Lys Thr Lys Leu Asn Ile Tyr Asn Ile Glu Phe Leu Leu Phe Val
 1               5                  10                  15

Phe Leu Val Trp Asp Pro Ala Arg Leu Val Leu Ala Asn Ile Gln Glu
            20                  25                  30

Asp Glu Ala Lys Asn Asn Ile Thr Ile Phe Thr Arg Ile Leu Asp Arg
        35                  40                  45

Leu Leu Asp Gly Tyr Asp Asn Arg Leu Arg Pro Gly Leu Gly Asp Ser
    50                  55                  60

Ile Thr Glu Val Phe Thr Asn Ile Tyr Val Thr Ser Phe Gly Pro Val
65                  70                  75                  80

Ser Asp Thr Asp Met Glu Tyr Thr Ile Asp Val Phe Phe Arg Gln Lys
                85                  90                  95

Trp Lys Asp Glu Arg Leu Lys Phe Lys Gly Pro Met Asn Ile Leu Arg
            100                 105                 110

Leu Asn Asn Leu Met Ala Ser Lys Ile Trp Thr Pro Asp Thr Phe Phe
        115                 120                 125

His Asn Gly Lys Lys Ser Val Ala His Asn Met Thr Met Pro Asn Lys
    130                 135                 140

Leu Leu Arg Ile Gln Asp Asp Gly Thr Leu Leu Tyr Thr Met Arg Leu
145                 150                 155                 160

Thr Val Gln Ala Glu Cys Pro Met His Leu Glu Asp Phe Pro Met Asp
                165                 170                 175

Ala His Ser Cys Pro Leu Lys Phe Gly Ser Tyr Ala Tyr Thr Thr Ser
            180                 185                 190

Glu Val Thr Tyr Ile Trp Thr Tyr Asn Ala Ser Asp Ser Val Gln Val
        195                 200                 205

Ala Pro Asp Gly Ser Arg Leu Asn Gln Tyr Asp Leu Leu Gly Gln Ser
    210                 215                 220

Ile Gly Lys Glu Thr Ile Lys Ser Ser Thr Gly Glu Tyr Thr Val Met
```

```
                225                             230                            235                            240
        Thr Ala His Phe His Leu Lys Arg Lys Ile Gly Tyr Phe Val Ile Gln
                        245                    250                    255

Thr Tyr Leu Pro Cys Ile Met Thr Val Ile Leu Ser Gln Val Ser Phe
                        260                    265                    270

Trp Leu Asn Arg Glu Ser Val Pro Ala Arg Thr Val Phe Gly Val Thr
                        275                    280                    285

Thr Val Leu Thr Met Thr Thr Leu Ser Ile Ser Ala Arg Asn Ser Leu
                        290                    295                    300

Pro Lys Val Ala Tyr Ala Thr Ala Met Asp Trp Phe Ile Ala Val Cys
        305                    310                    315                    320

Tyr Ala Phe Val Phe Ser Ala Leu Ile Glu Phe Ala Thr Val Asn Tyr
                        325                    330                    335

Phe Thr Lys Arg Gly Trp Thr Trp Asp Gly Lys Ser Val Val Asn Asp
                        340                    345                    350

Lys Lys Lys Glu Lys Ala Ser Val Met Ile Gln Asn Asn Ala Tyr Ala
                        355                    360                    365

Val Ala Val Ala Asn Tyr Ala Pro Asn Leu Ser Lys Asp Pro Val Leu
        370                    375                    380

Ser Thr Ile Ser Lys Ser Ala Thr Thr Pro Glu Pro Asn Lys Lys Pro
        385                    390                    395                    400

Glu Asn Lys Pro Ala Glu Ala Lys Lys Thr Phe Asn Ser Val Ser Lys
                        405                    410                    415

Ile Asp Arg Met Ser Arg Ile Val Phe Pro Val Leu Phe Gly Thr Phe
                        420                    425                    430

Asn Leu Val Tyr Trp Ala Thr Tyr Leu Asn Arg Glu Pro Val Leu Gly
                        435                    440                    445

Val Ser Pro
        450
```

( 2 ) INFORMATION FOR SEQ ID NO:13:

( i ) SEQUENCE CHARACTERISTICS:
        ( A ) LENGTH: 1638 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Coding Sequence
        ( B ) LOCATION: 87...1562
        ( D ) OTHER INFORMATION:

( x i ) SEQUENCE DESCRIPTION: SEQ ID NO:13:

```
GAATTCCCTT GTTTCAGTTC ATTCATCCTT CTCTCCTTTC CGCTCAGACT GTAGAGCTCG        60

GTCTCTCCAA GTTTGTGCCT AAGAAG ATG ATA ATC ACA CAA ACA AGT CAC TGT        113
                             Met Ile Ile Thr Gln Thr Ser His Cys
                              1                 5

TAC ATG ACC AGC CTT GGG ATT CTT TTC CTG ATT AAT ATT CTC CCT GGA         161
Tyr Met Thr Ser Leu Gly Ile Leu Phe Leu Ile Asn Ile Leu Pro Gly
 10              15                      20                  25

ACC ACT GGT CAA GGG GAA TCA AGA CGA CAA GAA CCC GGG GAC TTT GTG         209
Thr Thr Gly Gln Gly Glu Ser Arg Arg Gln Glu Pro Gly Asp Phe Val
                 30                      35                  40

AAG CAG GAC ATT GGC GGG CTG TCT CCT AAG CAT GCC CCA GAT ATT CCT         257
Lys Gln Asp Ile Gly Gly Leu Ser Pro Lys His Ala Pro Asp Ile Pro
                 45                      50                  55
```

-continued

| | | | | | | | | | | | | | | | | |
|---|---|---|---|---|---|---|---|---|---|---|---|---|---|---|---|---|
| GAT | GAC | AGC | ACT | GAC | AAC | ATC | ACT | ATC | TTC | ACC | AGA | ATC | TTG | GAT | CGT | 305 |
| Asp | Asp | Ser 60 | Thr | Asp | Asn | Ile 65 | Thr | Ile | Phe | Thr | Arg | Ile 70 | Leu | Asp | Arg | |
| CTT | CTG | GAC | GGC | TAT | GAC | AAC | CGG | CTG | CGA | CCT | GGG | CTT | GGA | GAT | GCA | 353 |
| Leu | Leu 75 | Asp | Gly | Tyr | Asp | Asn 80 | Arg | Leu | Arg | Pro | Gly 85 | Leu | Gly | Asp | Ala | |
| GTG | ACT | GAA | GTG | AAG | ACT | GAC | ATC | TAC | GTG | ACC | AGT | TTT | GGC | CCT | GTG | 401 |
| Val 90 | Thr | Glu | Val | Lys | Thr 95 | Asp | Ile | Tyr | Val | Thr 100 | Ser | Phe | Gly | Pro | Val 105 | |
| TCA | GAC | ACT | GAC | ATG | GAG | TAC | ACT | ATT | GAT | GTA | TTT | TTT | CGG | CAG | ACA | 449 |
| Ser | Asp | Thr | Asp | Met 110 | Glu | Tyr | Thr | Ile | Asp 115 | Val | Phe | Phe | Arg | Gln 120 | Thr | |
| TGG | CAT | GAT | GAA | AGA | CTG | AAA | TTT | GAT | GGC | CCC | ATG | AAG | ATC | CTT | CCA | 497 |
| Trp | His | Asp | Glu | Arg 125 | Leu | Lys | Phe | Asp | Gly 130 | Pro | Met | Lys | Ile | Leu 135 | Pro | |
| CTG | AAC | AAT | CTC | CTG | GCT | AGT | AAG | ATC | TGG | ACA | CCG | GAC | ACC | TTC | TTC | 545 |
| Leu | Asn | Asn | Leu 140 | Leu | Ala | Ser | Lys | Ile 145 | Trp | Thr | Pro | Asp | Thr 150 | Phe | Phe | |
| CAC | AAT | GGC | AAG | AAA | TCA | GTG | GCT | CAT | AAC | ATG | ACC | ACG | CCC | AAC | AAG | 593 |
| His | Asn | Gly | Lys 155 | Lys | Ser | Val | Ala | His 160 | Asn | Met | Thr | Thr | Pro 165 | Asn | Lys | |
| CTG | CTC | AGA | TTG | GTG | GAC | AAC | GGA | ACC | CTC | CTC | TAT | ACA | ATG | AGG | TTA | 641 |
| Leu 170 | Leu | Arg | Leu | Val | Asp 175 | Asn | Gly | Thr | Leu | Leu 180 | Tyr | Thr | Met | Arg | Leu 185 | |
| ACA | ATT | CAT | GCT | GAG | TGT | CCC | ATG | CAT | TTG | GAA | GAT | TTT | CCC | ATG | GAT | 689 |
| Thr | Ile | His | Ala | Glu 190 | Cys | Pro | Met | His | Leu 195 | Glu | Asp | Phe | Pro | Met 200 | Asp | |
| GTG | CAT | GCC | TGC | CCA | CTG | AAG | TTT | GGA | AGC | TAT | GCC | TAT | ACA | ACA | GCT | 737 |
| Val | His | Ala | Cys 205 | Pro | Leu | Lys | Phe | Gly 210 | Ser | Tyr | Ala | Tyr | Thr 215 | Thr | Ala | |
| GAA | GTG | GTT | TAT | TCT | TGG | ACT | CTC | GGA | AAG | AAC | AAA | TCC | GTG | GAA | GTG | 785 |
| Glu | Val | Val | Tyr 220 | Ser | Trp | Thr | Leu | Gly 225 | Lys | Asn | Lys | Ser | Val 230 | Glu | Val | |
| GCA | CAG | GAT | GGT | TCT | CGC | TTG | AAC | CAG | TAT | GAC | CTT | TTG | GGC | CAT | GTT | 833 |
| Ala | Gln | Asp 235 | Gly | Ser | Arg | Leu | Asn 240 | Gln | Tyr | Asp | Leu | Leu 245 | Gly | His | Val | |
| GTT | GGG | ACA | GAG | ATA | ATC | CGG | TCT | AGT | ACA | GGA | GAA | TAT | GTC | GTC | ATG | 881 |
| Val 250 | Gly | Thr | Glu | Ile | Ile 255 | Arg | Ser | Ser | Thr | Gly 260 | Glu | Tyr | Val | Val | Met 265 | |
| ACA | ACC | CAC | TTC | CAT | CTC | AAG | CGA | AAA | ATT | GGC | TAC | TTT | GTG | ATC | CAG | 929 |
| Thr | Thr | His | Phe | His 270 | Leu | Lys | Arg | Lys | Ile 275 | Gly | Tyr | Phe | Val | Ile 280 | Gln | |
| ACC | TAC | TTG | CCA | TGT | ATC | ATG | ACT | GTC | ATT | CTG | TCA | CAA | GTG | TCG | TTC | 977 |
| Thr | Tyr | Leu | Pro 285 | Cys | Ile | Met | Thr | Val 290 | Ile | Leu | Ser | Gln | Val 295 | Ser | Phe | |
| TGG | CTC | AAC | AGA | GAG | TCT | GTT | CCT | GCC | CGT | ACA | GTC | TTT | GGT | GTC | ACC | 1025 |
| Trp | Leu | Asn | Arg 300 | Glu | Ser | Val | Pro | Ala 305 | Arg | Thr | Val | Phe | Gly 310 | Val | Thr | |
| ACT | GTG | CTT | ACC | ATG | ACC | ACC | TTG | AGT | ATC | AGT | GCC | AGA | AAT | TCC | TTA | 1073 |
| Thr | Val | Leu 315 | Thr | Met | Thr | Thr | Leu 320 | Ser | Ile | Ser | Ala | Arg 325 | Asn | Ser | Leu | |
| CCT | AAA | GTG | GCA | TAT | GCG | ACG | GCC | ATG | GAC | TGG | TTC | ATA | GCC | GTC | TGT | 1121 |
| Pro 330 | Lys | Val | Ala | Tyr | Ala 335 | Thr | Ala | Met | Asp | Trp 340 | Phe | Ile | Ala | Val | Cys 345 | |
| TAT | GCC | TTT | GTA | TTT | TCT | GCA | CTG | ATT | GAA | TTT | GCC | ACT | GTC | AAC | TAT | 1169 |
| Tyr | Ala | Phe | Val | Phe 350 | Ser | Ala | Leu | Ile | Glu 355 | Phe | Ala | Thr | Val | Asn 360 | Tyr | |
| TTC | ACC | AAG | CGG | AGT | TGG | GCT | TGG | GAA | GGC | AAG | AAG | GTG | CCA | GAG | GCC | 1217 |
| Phe | Thr | Lys | Arg 365 | Ser | Trp | Ala | Trp | Glu 370 | Gly | Lys | Lys | Val | Pro 375 | Glu | Ala | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CTG | GAG | ATG | AAG | AAG | AAA | ACA | CCA | GCA | GCC | CCA | GCA | AAG | AAA | ACC | AGC | 1265 |
| Leu | Glu | Met<br>380 | Lys | Lys | Lys | Thr | Pro<br>385 | Ala | Ala | Pro | Ala | Lys<br>390 | Lys | Thr | Ser |  |
| ACT | ACC | TTC | AAC | ATC | GTG | GGG | ACC | ACC | TAT | CCC | ATC | AAC | CTG | GCC | AAG | 1313 |
| Thr | Thr<br>395 | Phe | Asn | Ile | Val | Gly<br>400 | Thr | Thr | Tyr | Pro | Ile<br>405 | Asn | Leu | Ala | Lys |  |
| GAC | ACT | GAA | TTT | TCC | ACC | ATC | TCC | AAG | GGC | GCT | GCT | CCC | AGT | GCC | TCC | 1361 |
| Asp | Thr<br>410 | Glu | Phe | Ser | Thr<br>415 | Ile | Ser | Lys | Gly | Ala<br>420 | Ala | Pro | Ser | Ala | Ser<br>425 |  |
| TCA | ACC | CCA | ACA | ATC | ATT | GCT | TCA | CCC | AAG | GCC | ACC | TAC | GTG | CAG | GAC | 1409 |
| Ser | Thr | Pro | Thr | Ile<br>430 | Ile | Ala | Ser | Pro | Lys<br>435 | Ala | Thr | Tyr | Val | Gln<br>440 | Asp |  |
| AGC | CCG | ACT | GAG | ACC | AAG | ACC | TAC | AAC | AGT | GTC | AGC | AAG | GTT | GAC | AAA | 1457 |
| Ser | Pro | Thr | Glu<br>445 | Thr | Lys | Thr | Tyr | Asn<br>450 | Ser | Val | Ser | Lys<br>455 | Val | Asp | Lys |  |
| ATT | TCC | CGC | ATC | ATC | TTT | CCT | GTG | CTC | TTT | GCC | ATA | TTC | AAT | CTG | GTC | 1505 |
| Ile | Ser | Arg<br>460 | Ile | Ile | Phe | Pro | Val<br>465 | Leu | Phe | Ala | Ile | Phe<br>470 | Asn | Leu | Val |  |
| TAT | TGG | GCC | ACA | TAT | GTC | AAC | CGG | GAG | TCA | GCT | ATC | AAG | GGC | ATG | ATC | 1553 |
| Tyr | Trp | Ala<br>475 | Thr | Tyr | Val | Asn | Arg<br>480 | Glu | Ser | Ala | Ile | Lys<br>485 | Gly | Met | Ile |  |
| CGC | AAA | CAG | TAGATAGTGG | CAGTGCAGCA | ACCAGAGCAC | TGTATACCCC | GTGAAGCATC |  |  |  |  |  |  |  |  | 1612 |
| Arg | Lys | Gln<br>490 |  |  |  |  |  |  |  |  |  |  |  |  |  |  |

CAGGCACCCA AACCCCGGGG CTCCCC                                           1638

( 2 ) INFORMATION FOR SEQ ID NO:14:

( i ) SEQUENCE CHARACTERISTICS:
        ( A ) LENGTH: 492 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:14:

| Met<br>1 | Ile | Ile | Thr | Gln<br>5 | Thr | Ser | His | Cys | Tyr<br>10 | Met | Thr | Ser | Leu | Gly<br>15 | Ile |
|---|---|---|---|---|---|---|---|---|---|---|---|---|---|---|---|
| Leu | Phe | Leu | Ile<br>20 | Asn | Ile | Leu | Pro | Gly<br>25 | Thr | Thr | Gly | Gln | Gly<br>30 | Glu | Ser |
| Arg | Arg | Gln<br>35 | Glu | Pro | Gly | Asp | Phe<br>40 | Val | Lys | Gln | Asp | Ile<br>45 | Gly | Gly | Leu |
| Ser | Pro<br>50 | Lys | His | Ala | Pro | Asp<br>55 | Ile | Pro | Asp | Asp | Ser<br>60 | Thr | Asp | Asn | Ile |
| Thr<br>65 | Ile | Phe | Thr | Arg | Ile<br>70 | Leu | Asp | Arg | Leu | Leu<br>75 | Asp | Gly | Tyr | Asp | Asn<br>80 |
| Arg | Leu | Arg | Pro | Gly<br>85 | Leu | Gly | Asp | Ala | Val<br>90 | Thr | Glu | Val | Lys | Thr<br>95 | Asp |
| Ile | Tyr | Val | Thr<br>100 | Ser | Phe | Gly | Pro | Val<br>105 | Ser | Asp | Thr | Asp | Met<br>110 | Glu | Tyr |
| Thr | Ile | Asp | Val<br>115 | Phe | Phe | Arg | Gln | Thr<br>120 | Trp | His | Asp | Glu | Arg<br>125 | Leu | Lys |
| Phe | Asp<br>130 | Gly | Pro | Met | Lys | Ile<br>135 | Leu | Pro | Leu | Asn | Asn<br>140 | Leu | Leu | Ala | Ser |
| Lys<br>145 | Ile | Trp | Thr | Pro | Asp<br>150 | Thr | Phe | Phe | His | Asn<br>155 | Gly | Lys | Lys | Ser | Val<br>160 |
| Ala | His | Asn | Met | Thr | Thr | Pro | Asn | Lys | Leu | Leu | Arg | Leu | Val | Asp | Asn |

-continued

|     |     |     | 165 |     |     |     | 170 |     |     |     | 175 |     |
|-----|-----|-----|-----|-----|-----|-----|-----|-----|-----|-----|-----|-----|

Gly Thr Leu Leu Tyr Thr Met Arg Leu Thr Ile His Ala Glu Cys Pro
            180             185             190

Met His Leu Glu Asp Phe Pro Met Asp Val His Ala Cys Pro Leu Lys
        195             200             205

Phe Gly Ser Tyr Ala Tyr Thr Thr Ala Glu Val Val Tyr Ser Trp Thr
    210             215             220

Leu Gly Lys Asn Lys Ser Val Glu Val Ala Gln Asp Gly Ser Arg Leu
225             230             235             240

Asn Gln Tyr Asp Leu Leu Gly His Val Val Gly Thr Glu Ile Ile Arg
            245             250             255

Ser Ser Thr Gly Glu Tyr Val Val Met Thr Thr His Phe His Leu Lys
        260             265             270

Arg Lys Ile Gly Tyr Phe Val Ile Gln Thr Tyr Leu Pro Cys Ile Met
        275             280             285

Thr Val Ile Leu Ser Gln Val Ser Phe Trp Leu Asn Arg Glu Ser Val
    290             295             300

Pro Ala Arg Thr Val Phe Gly Val Thr Thr Val Leu Thr Met Thr Thr
305             310             315             320

Leu Ser Ile Ser Ala Arg Asn Ser Leu Pro Lys Val Ala Tyr Ala Thr
                325             330             335

Ala Met Asp Trp Phe Ile Ala Val Cys Tyr Ala Phe Val Phe Ser Ala
            340             345             350

Leu Ile Glu Phe Ala Thr Val Asn Tyr Phe Thr Lys Arg Ser Trp Ala
        355             360             365

Trp Glu Gly Lys Lys Val Pro Glu Ala Leu Glu Met Lys Lys Lys Thr
    370             375             380

Pro Ala Ala Pro Ala Lys Lys Thr Ser Thr Thr Phe Asn Ile Val Gly
385             390             395             400

Thr Thr Tyr Pro Ile Asn Leu Ala Lys Asp Thr Glu Phe Ser Thr Ile
            405             410             415

Ser Lys Gly Ala Ala Pro Ser Ala Ser Ser Thr Pro Thr Ile Ile Ala
        420             425             430

Ser Pro Lys Ala Thr Tyr Val Gln Asp Ser Pro Thr Glu Thr Lys Thr
    435             440             445

Tyr Asn Ser Val Ser Lys Val Asp Lys Ile Ser Arg Ile Ile Phe Pro
450             455             460

Val Leu Phe Ala Ile Phe Asn Leu Val Tyr Trp Ala Thr Tyr Val Asn
465             470             475             480

Arg Glu Ser Ala Ile Lys Gly Met Ile Arg Lys Gln
            485             490

( 2 ) INFORMATION FOR SEQ ID NO:15:

( i ) SEQUENCE CHARACTERISTICS:
        ( A ) LENGTH: 2310 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Coding Sequence
        ( B ) LOCATION: 298...1683
        ( D ) OTHER INFORMATION:

( x i ) SEQUENCE DESCRIPTION: SEQ ID NO:15:

```
GAATTCCCCC CTTGCAGGCC GAGCCGGGGC CCTGCGCCCT CCCCCTCCGC CCAGCTCGGC      60

CAAGGGCGCA TTTGCTGAGC GTCTGGCGGC CTCTACCGGA GCACCTCTGC AGAGGGCCGA     120

TCCTCCAGCC CAGAGACGAC ATGTGGCGCT CGGGCGAGTG CCTTGCAGAG AGAGGAGTAG     180

CTTGCTGGCT TTGAACGCGT GGCGTGGCAG ATATTTCAGA AAGCTTCAAG AACAAGCTGG     240

AGAAGGGAAG AGTTATTCCT CCATATTCAC CTGCTTCAAC TACTATTCTT ATTGGGA ATG   300
                                                                Met
                                                                  1
```

| | | | | | | | | | | | | | | | | |
|---|---|---|---|---|---|---|---|---|---|---|---|---|---|---|---|---|
| GAC | AAT | GGA | ATG | TTC | TCT | GGT | TTT | ATC | ATG | ATC | AAA | AAC | CTC | CTT | CTC | 348 |
| Asp | Asn | Gly | Met | Phe | Ser | Gly | Phe | Ile | Met | Ile | Lys | Asn | Leu | Leu | Leu | |
| | | 5 | | | | | 10 | | | | | 15 | | | | |
| TTT | TGT | ATT | TCC | ATG | AAC | TTA | TCC | AGT | CAC | TTT | GGC | TTT | TCA | CAG | ATG | 396 |
| Phe | Cys | Ile | Ser | Met | Asn | Leu | Ser | Ser | His | Phe | Gly | Phe | Ser | Gln | Met | |
| | | 20 | | | | 25 | | | | 30 | | | | | | |
| CCA | ACC | AGT | TCA | GTG | AAA | GAT | GAG | ACC | AAT | GAC | AAC | ATC | ACG | ATA | TTT | 444 |
| Pro | Thr | Ser | Ser | Val | Lys | Asp | Glu | Thr | Asn | Asp | Asn | Ile | Thr | Ile | Phe | |
| | 35 | | | | 40 | | | | 45 | | | | | | | |
| ACC | AGG | ATC | TTG | GAT | GGG | CTC | TTG | GAT | GGC | TAC | GAC | AAC | AGA | CTT | CGG | 492 |
| Thr | Arg | Ile | Leu | Asp | Gly | Leu | Leu | Asp | Gly | Tyr | Asp | Asn | Arg | Leu | Arg | |
| 50 | | | | | 55 | | | | 60 | | | | | 65 | | |
| CCC | GGG | CTG | GGA | GAG | CGC | ATC | ACT | CAG | GTG | AGG | ACC | GAC | ATC | TAC | GTC | 540 |
| Pro | Gly | Leu | Gly | Glu | Arg | Ile | Thr | Gln | Val | Arg | Thr | Asp | Ile | Tyr | Val | |
| | | | 70 | | | | | 75 | | | | | 80 | | | |
| ACC | AGC | TTC | GGC | CCG | GTG | TCC | GAC | ACG | GAA | ATG | GAG | TAC | ACC | ATA | GAC | 588 |
| Thr | Ser | Phe | Gly | Pro | Val | Ser | Asp | Thr | Glu | Met | Glu | Tyr | Thr | Ile | Asp | |
| | | | 85 | | | | 90 | | | | | 95 | | | | |
| GTG | TTT | TTC | CGA | CAA | AGC | TGG | AAA | GAT | GAA | AGG | CTT | CGG | TTT | AAG | GGG | 636 |
| Val | Phe | Phe | Arg | Gln | Ser | Trp | Lys | Asp | Glu | Arg | Leu | Arg | Phe | Lys | Gly | |
| | | 100 | | | | | 105 | | | | | 110 | | | | |
| CCC | ATG | CAG | CGC | CTC | CCT | CTC | AAC | AAC | CTC | CTT | GCC | AGC | AAG | ATC | TGG | 684 |
| Pro | Met | Gln | Arg | Leu | Pro | Leu | Asn | Asn | Leu | Leu | Ala | Ser | Lys | Ile | Trp | |
| | 115 | | | | | 120 | | | | | 125 | | | | | |
| ACC | CCA | GAC | ACG | TTC | TTC | CAC | AAC | GGG | AAG | AAG | TCC | ATC | GCT | CAC | AAC | 732 |
| Thr | Pro | Asp | Thr | Phe | Phe | His | Asn | Gly | Lys | Lys | Ser | Ile | Ala | His | Asn | |
| 130 | | | | | 135 | | | | 140 | | | | | 145 | | |
| ATG | ACC | ACG | CCC | AAC | AAG | CTG | CTG | CGG | CTG | GAG | GAC | GAC | GGC | ACC | CTG | 780 |
| Met | Thr | Thr | Pro | Asn | Lys | Leu | Leu | Arg | Leu | Glu | Asp | Asp | Gly | Thr | Leu | |
| | | | | 150 | | | | 155 | | | | | 160 | | | |
| CTC | TAC | ACC | ATG | CGC | TTG | ACC | ATC | TCT | GCA | GAG | TGC | CCC | ATG | CAG | CTT | 828 |
| Leu | Tyr | Thr | Met | Arg | Leu | Thr | Ile | Ser | Ala | Glu | Cys | Pro | Met | Gln | Leu | |
| | | | 165 | | | | 170 | | | | | 175 | | | | |
| GAG | GAC | TTC | CCG | ATG | GAT | GCG | CAC | GCT | TGC | CCT | CTG | AAA | TTT | GGC | AGC | 876 |
| Glu | Asp | Phe | Pro | Met | Asp | Ala | His | Ala | Cys | Pro | Leu | Lys | Phe | Gly | Ser | |
| | | 180 | | | | | 185 | | | | | 190 | | | | |
| TAT | GCG | TAC | CCT | AAT | TCT | GAA | GTC | GTT | TAC | GTC | TGG | ACC | AAC | GGC | TCC | 924 |
| Tyr | Ala | Tyr | Pro | Asn | Ser | Glu | Val | Val | Tyr | Val | Trp | Thr | Asn | Gly | Ser | |
| | 195 | | | | | 200 | | | | | 205 | | | | | |
| ACC | AAG | TCG | GTG | GTG | GTG | GCG | GAA | GAT | GGC | TCC | AGA | CTG | AAC | CAG | TAC | 972 |
| Thr | Lys | Ser | Val | Val | Val | Ala | Glu | Asp | Gly | Ser | Arg | Leu | Asn | Gln | Tyr | |
| 210 | | | | | 215 | | | | | 220 | | | | | 225 | |
| CAC | CTG | ATG | GGG | CAG | ACG | GTG | GGC | ACT | GAG | AAC | ATC | AGC | ACC | AGC | ACA | 1020 |
| His | Leu | Met | Gly | Gln | Thr | Val | Gly | Thr | Glu | Asn | Ile | Ser | Thr | Ser | Thr | |
| | | | 230 | | | | | 235 | | | | | 240 | | | |
| GGC | GAA | TAC | ACA | ATC | ATG | ACA | GCT | CAC | TTC | CAC | CTG | AAA | AGG | AAG | ATT | 1068 |
| Gly | Glu | Tyr | Thr | Ile | Met | Thr | Ala | His | Phe | His | Leu | Lys | Arg | Lys | Ile | |
| | | | 245 | | | | 250 | | | | | 255 | | | | |
| GGC | TAC | TTT | GTC | ATC | CAG | ACC | TAC | CTT | CCC | TGC | ATA | ATG | ACC | GTG | ATC | 1116 |
| Gly | Tyr | Phe | Val | Ile | Gln | Thr | Tyr | Leu | Pro | Cys | Ile | Met | Thr | Val | Ile | |
| | | 260 | | | | | 265 | | | | | 270 | | | | |

```
TTA TCA CAG GTG TCC TTT TGG CTG AAC CGG GAA TCA GTC CCA GCC AGG       1164
Leu Ser Gln Val Ser Phe Trp Leu Asn Arg Glu Ser Val Pro Ala Arg
    275             280                 285

ACA GTT TTT GGG GTC ACC ACG GTG CTG ACC ATG ACG ACC CTC AGC ATC       1212
Thr Val Phe Gly Val Thr Thr Val Leu Thr Met Thr Thr Leu Ser Ile
290             295                 300                 305

AGC GCC AGG AAC TCT CTG CCC AAA GTG GCC TAC GCC ACC GCC ATG GAC       1260
Ser Ala Arg Asn Ser Leu Pro Lys Val Ala Tyr Ala Thr Ala Met Asp
                310                 315                 320

TGG TTC ATA GCT GTG TGC TAT GCC TTC GTC TTC TCG GCG CTG ATA GAG       1308
Trp Phe Ile Ala Val Cys Tyr Ala Phe Val Phe Ser Ala Leu Ile Glu
            325                 330                 335

TTT GCC ACG GTC AAT TAC TTT ACC AAG AGA GGC TGG GCC TGG GAT GGC       1356
Phe Ala Thr Val Asn Tyr Phe Thr Lys Arg Gly Trp Ala Trp Asp Gly
        340                 345                 350

AAA AAA GCC TTG GAA GCA GCC AAG ATC AAG AAA AAG CGT GAA GTC ATA       1404
Lys Lys Ala Leu Glu Ala Ala Lys Ile Lys Lys Lys Arg Glu Val Ile
    355                 360                 365

CTA AAT AAG TCA ACA AAC GCT TTT ACA ACT GGG AAG ATG TCT CAC CCC       1452
Leu Asn Lys Ser Thr Asn Ala Phe Thr Thr Gly Lys Met Ser His Pro
370                 375                 380                 385

CCA AAC ATT CCG AAG GAA CAG ACC CCA GCA GGG ACG TCG AAT ACA ACC       1500
Pro Asn Ile Pro Lys Glu Gln Thr Pro Ala Gly Thr Ser Asn Thr Thr
                390                 395                 400

TCA GTC TCA GTA AAA CCC TCT GAA GAG AAG ACT TCT GAA AGC AAA AAG       1548
Ser Val Ser Val Lys Pro Ser Glu Glu Lys Thr Ser Glu Ser Lys Lys
            405                 410                 415

ACT TAC AAC AGT ATC AGC AAA ATT GAC AAA ATG TCC CGA ATC GTA TTC       1596
Thr Tyr Asn Ser Ile Ser Lys Ile Asp Lys Met Ser Arg Ile Val Phe
        420                 425                 430

CCA GTC TTG TTC GGC ACT TTC AAC TTA GTT TAC TGG GCA ACG TAT TTG       1644
Pro Val Leu Phe Gly Thr Phe Asn Leu Val Tyr Trp Ala Thr Tyr Leu
    435                 440                 445

AAT AGG GAG CCG GTG ATA AAA GGA GCC GCC TCT CCA AAA TAACCGGCCA CAC    1696
Asn Arg Glu Pro Val Ile Lys Gly Ala Ala Ser Pro Lys
450                 455                 460

TCCCAAACTC CAAGACAGCC ATACTTCCAG CGAAATGGTA CCAAGGAGAG GTTTTGCTCA     1756

CAGGGACTCT CCATATGTGA GCACTATCTT TCAGGAAATT TTGCATGTT TAATAATATG      1816

TACAAATAAT ATTGCCTTGA TGTTTCTATA TGTAACTTCA GATGTTTCCA AGATGTCCCA     1876

TTGATAATTC GAGCAAACAA CTTTCTGGAA AAACAGGATA CGATGACTGA CACTCAGATG     1936

CCCAGTATCA TACGTTGATA GTTACAAAC AAGATACGTA TATTTTAAC TGCTTCAAGT       1996

GTTACCTAAC AATGTTTTTT ATACTTCAAA TGTCATTTCA TACAAATTTT CCCAGTGAAT     2056

AAATATTTTA GGAAACTCTC CATGATTATT AGAAGACCAA CTATATTGCG AGAAACAGAG     2116

ATCATAAAGA GCACGTTTTC CATTATGAGG AAACTTGGAC ATTTATGTAC AAAATGAATT     2176

GCCTTTGATA ATTCTTACTG TTCTGAAATT AGGAAAGTAC TTGCATGATC TTACACGAAG     2236

AAATAGAATA GGCAAACTTT TATGTAGGCA GATTAATAAC AGAAATACAT CATATGTTAG     2296

ATACACAAAA TATT                                                       2310
```

( 2 ) INFORMATION FOR SEQ ID NO:16:

( i ) SEQUENCE CHARACTERISTICS:
        ( A ) LENGTH: 462 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:16:

```
Met  Asp  Asn  Gly  Met  Phe  Ser  Gly  Phe  Ile  Met  Ile  Lys  Asn  Leu  Leu
 1             5                    10                       15
Leu  Phe  Cys  Ile  Ser  Met  Asn  Leu  Ser  Ser  His  Phe  Gly  Phe  Ser  Gln
              20                   25                       30
Met  Pro  Thr  Ser  Ser  Val  Lys  Asp  Glu  Thr  Asn  Asp  Asn  Ile  Thr  Ile
              35                   40                       45
Phe  Thr  Arg  Ile  Leu  Asp  Gly  Leu  Leu  Asp  Gly  Tyr  Asp  Asn  Arg  Leu
         50                   55                   60
Arg  Pro  Gly  Leu  Gly  Glu  Arg  Ile  Thr  Gln  Val  Arg  Thr  Asp  Ile  Tyr
 65                  70                   75                            80
Val  Thr  Ser  Phe  Gly  Pro  Val  Ser  Asp  Thr  Glu  Met  Glu  Tyr  Thr  Ile
                   85                   90                       95
Asp  Val  Phe  Phe  Arg  Gln  Ser  Trp  Lys  Asp  Glu  Arg  Leu  Arg  Phe  Lys
                  100                  105                      110
Gly  Pro  Met  Gln  Arg  Leu  Pro  Leu  Asn  Asn  Leu  Leu  Ala  Ser  Lys  Ile
              115                  120                      125
Trp  Thr  Pro  Asp  Thr  Phe  Phe  His  Asn  Gly  Lys  Lys  Ser  Ile  Ala  His
     130                       135                 140
Asn  Met  Thr  Thr  Pro  Asn  Lys  Leu  Leu  Arg  Leu  Glu  Asp  Asp  Gly  Thr
145                       150                  155                      160
Leu  Leu  Tyr  Thr  Met  Arg  Leu  Thr  Ile  Ser  Ala  Glu  Cys  Pro  Met  Gln
                   165                  170                       175
Leu  Glu  Asp  Phe  Pro  Met  Asp  Ala  His  Ala  Cys  Pro  Leu  Lys  Phe  Gly
              180                       185                      190
Ser  Tyr  Ala  Tyr  Pro  Asn  Ser  Glu  Val  Val  Tyr  Val  Trp  Thr  Asn  Gly
         195                       200                 205
Ser  Thr  Lys  Ser  Val  Val  Val  Ala  Glu  Asp  Gly  Ser  Arg  Leu  Asn  Gln
     210                       215                 220
Tyr  His  Leu  Met  Gly  Gln  Thr  Val  Gly  Thr  Glu  Asn  Ile  Ser  Thr  Ser
225                       230                  235                      240
Thr  Gly  Glu  Tyr  Thr  Ile  Met  Thr  Ala  His  Phe  His  Leu  Lys  Arg  Lys
                   245                       250                      255
Ile  Gly  Tyr  Phe  Val  Ile  Gln  Thr  Tyr  Leu  Pro  Cys  Ile  Met  Thr  Val
              260                       265                 270
Ile  Leu  Ser  Gln  Val  Ser  Phe  Trp  Leu  Asn  Arg  Glu  Ser  Val  Pro  Ala
         275                       280                 285
Arg  Thr  Val  Phe  Gly  Val  Thr  Thr  Val  Leu  Thr  Met  Thr  Thr  Leu  Ser
     290                       295                 300
Ile  Ser  Ala  Arg  Asn  Ser  Leu  Pro  Lys  Val  Ala  Tyr  Ala  Thr  Ala  Met
305                       310                  315                      320
Asp  Trp  Phe  Ile  Ala  Val  Cys  Tyr  Ala  Phe  Val  Phe  Ser  Ala  Leu  Ile
                   325                       330                      335
Glu  Phe  Ala  Thr  Val  Asn  Tyr  Phe  Thr  Lys  Arg  Gly  Trp  Ala  Trp  Asp
              340                       345                      350
Gly  Lys  Lys  Ala  Leu  Glu  Ala  Ala  Lys  Ile  Lys  Lys  Lys  Arg  Glu  Val
         355                       360                 365
Ile  Leu  Asn  Lys  Ser  Thr  Asn  Ala  Phe  Thr  Thr  Gly  Lys  Met  Ser  His
     370                       375                 380
Pro  Pro  Asn  Ile  Pro  Lys  Glu  Gln  Thr  Pro  Ala  Gly  Thr  Ser  Asn  Thr
385                       390                       395                 400
```

| | | | | | | | | | | | | | | |
|---|---|---|---|---|---|---|---|---|---|---|---|---|---|---|
|Thr|Ser|Val|Ser|Val|Lys|Pro|Ser|Glu|Glu|Lys|Thr|Ser|Glu|Ser|Lys|
| | | | |405| | | |410| | | | |415| |
|Lys|Thr|Tyr|Asn|Ser|Ile|Ser|Lys|Ile|Asp|Lys|Met|Ser|Arg|Ile|Val|
| | | |420| | | |425| | | | |430| | |
|Phe|Pro|Val|Leu|Phe|Gly|Thr|Phe|Asn|Leu|Val|Tyr|Trp|Ala|Thr|Tyr|
| | |435| | | |440| | | | |445| | | |
|Leu|Asn|Arg|Glu|Pro|Val|Ile|Lys|Gly|Ala|Ala|Ser|Pro|Lys|
| |450| | | | |455| | | |460| | | |

( 2 ) INFORMATION FOR SEQ ID NO:17:

( i ) SEQUENCE CHARACTERISTICS:
    ( A ) LENGTH: 1732 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: Coding Sequence
    ( B ) LOCATION: 27...1385
    ( D ) OTHER INFORMATION:

( x i ) SEQUENCE DESCRIPTION: SEQ ID NO:17:

```
AATTCTGCAT TTCAGTGCAC TGCAGG ATG GCG TCA TCT CTG CCC TGG CTG TGC        53
                            Met Ala Ser Ser Leu Pro Trp Leu Cys
                             1               5

ATT ATT CTG TGG CTA GAA AAT GCC CTA GGG AAA CTC GAA GTT GAA GGC        101
Ile Ile Leu Trp Leu Glu Asn Ala Leu Gly Lys Leu Glu Val Glu Gly
 10              15                  20                  25

AAC TTC TAC TCA GAA AAC GTC AGT CGG ATC CTG GAC AAC TTG CTT GAA        149
Asn Phe Tyr Ser Glu Asn Val Ser Arg Ile Leu Asp Asn Leu Leu Glu
             30                  35                  40

GGC TAT GAC AAT CGG CTG CGG CCG GGA TTT GGA GGT GCT GTC ACT GAA        197
Gly Tyr Asp Asn Arg Leu Arg Pro Gly Phe Gly Gly Ala Val Thr Glu
         45                  50                  55

GTC AAA ACA GAC ATT TAT GTG ACC AGT TTT GGG CCC GTG TCA GAT GTG        245
Val Lys Thr Asp Ile Tyr Val Thr Ser Phe Gly Pro Val Ser Asp Val
     60                  65                  70

GAG ATG GAG TAT ACG ATG GAT GTT TTT TTT CGC CAG ACC TGG ACT GAT        293
Glu Met Glu Tyr Thr Met Asp Val Phe Phe Arg Gln Thr Trp Thr Asp
 75                  80                  85

GAG AGG TTG AAG TTT GGG GGG CCA ACT GAG ATT CTG AGT CTG AAT AAT        341
Glu Arg Leu Lys Phe Gly Gly Pro Thr Glu Ile Leu Ser Leu Asn Asn
 90                  95                 100                 105

TTG ATG GTC AGT AAA ATC TGG ACG CCT GAC ACC TTT TTC AGA AAT GGT        389
Leu Met Val Ser Lys Ile Trp Thr Pro Asp Thr Phe Phe Arg Asn Gly
                 110                 115                 120

AAA AAG TCC ATT GCT CAC AAC ATG ACA ACT CCT AAT AAA CTC TTC AGA        437
Lys Lys Ser Ile Ala His Asn Met Thr Thr Pro Asn Lys Leu Phe Arg
                 125                 130                 135

ATA ATG CAG AAT GGA ACC ATT TTA TAC ACC ATG AGG CTT ACC ATC AAT        485
Ile Met Gln Asn Gly Thr Ile Leu Tyr Thr Met Arg Leu Thr Ile Asn
         140                 145                 150

GCT GAC TGT CCC ATG AGG CTG GTT AAC TTT CCT ATG GAT GGG CAT GCT        533
Ala Asp Cys Pro Met Arg Leu Val Asn Phe Pro Met Asp Gly His Ala
 155                 160                 165

TGT CCA CTC AAG TTT GGG AGC TAT GCT TAT CCC AAA AGT GAA ATC ATA        581
Cys Pro Leu Lys Phe Gly Ser Tyr Ala Tyr Pro Lys Ser Glu Ile Ile
 170                 175                 180                 185

TAT ACG TGG AAA AAA GGA CCA CTT TAC TCA GTA GAA GTC CCA GAA GAA        629
Tyr Thr Trp Lys Lys Gly Pro Leu Tyr Ser Val Glu Val Pro Glu Glu
```

```
             190                      195                     200
TCT TCA AGC CTT CTC CAG TAT GAT CTG ATT GGA CAA ACA GTA TCT AGT              677
Ser Ser Ser Leu Leu Gln Tyr Asp Leu Ile Gly Gln Thr Val Ser Ser
            205                 210                 215

GAG ACA ATT AAA TCT AAC ACA GGT GAA TAC GTT ATA ATG ACA GTT TAC              725
Glu Thr Ile Lys Ser Asn Thr Gly Glu Tyr Val Ile Met Thr Val Tyr
        220                 225                 230

TTC CAC TTG CAA AGG AAG ATG GGC TAC TTC ATG ATA CAG ATA TAC ACT              773
Phe His Leu Gln Arg Lys Met Gly Tyr Phe Met Ile Gln Ile Tyr Thr
    235                 240                 245

CCT TGC ATT ATG ACA GTC ATT CTT TCC CAG GTG TCT TTC TGG ATT AAT              821
Pro Cys Ile Met Thr Val Ile Leu Ser Gln Val Ser Phe Trp Ile Asn
250                 255                 260                 265

AAG GAG TCC GTC CCA GCA AGA ACT GTT CTT GGG ATC ACC ACT GTT TTA              869
Lys Glu Ser Val Pro Ala Arg Thr Val Leu Gly Ile Thr Thr Val Leu
                270                 275                 280

ACT ATG ACC ACT TTG AGC ATC AGT GCC CGG CAC TCT TTG CCA AAA GTG              917
Thr Met Thr Thr Leu Ser Ile Ser Ala Arg His Ser Leu Pro Lys Val
            285                 290                 295

TCA TAT GCC ACT GCC ATG GAT TGG TTC ATA GCT GTT TGC TTT GCA TTC              965
Ser Tyr Ala Thr Ala Met Asp Trp Phe Ile Ala Val Cys Phe Ala Phe
        300                 305                 310

GTC TTC TCT GCT CTT ATC GAG TTC GCA GCT GTC AAC TAC TTT ACC AAT              1013
Val Phe Ser Ala Leu Ile Glu Phe Ala Ala Val Asn Tyr Phe Thr Asn
    315                 320                 325

CTT CAG ACA CAG AAG GCG AAA AGG AAG GCA CAG TTT GCA GCC CCA CCC              1061
Leu Gln Thr Gln Lys Ala Lys Arg Lys Ala Gln Phe Ala Ala Pro Pro
330                 335                 340                 345

ACA GTG ACA ATA TCA AAA GCT ACT GAA CCT TTG GAA GCT GAG ATT GTT              1109
Thr Val Thr Ile Ser Lys Ala Thr Glu Pro Leu Glu Ala Glu Ile Val
                350                 355                 360

TTG CAT CCT GAC TCC AAA TAT CAT CTG AAG AAA AGG ATC ACT TCT CTG              1157
Leu His Pro Asp Ser Lys Tyr His Leu Lys Lys Arg Ile Thr Ser Leu
            365                 370                 375

TCT TTG CCA ATA GTT TCA TCT TCC GAG GCC AAT AAA GTG CTC ACG AGA              1205
Ser Leu Pro Ile Val Ser Ser Ser Glu Ala Asn Lys Val Leu Thr Arg
        380                 385                 390

GCG CCC ATC TTA CAA TCA ACA CCT GTC ACA CCC CCA CCA CTC CCG CCA              1253
Ala Pro Ile Leu Gln Ser Thr Pro Val Thr Pro Pro Pro Leu Pro Pro
    395                 400                 405

GCC TTT GGA GGC ACC AGT AAA ATA GAC CAG TAT TCT CGA ATT CTC TTC              1301
Ala Phe Gly Gly Thr Ser Lys Ile Asp Gln Tyr Ser Arg Ile Leu Phe
410                 415                 420                 425

CCA GTT GCA TTT GCA GGA TTC AAC CTT GTG TAC TGG GTA GTT TAT CTT              1349
Pro Val Ala Phe Ala Gly Phe Asn Leu Val Tyr Trp Val Val Tyr Leu
                430                 435                 440

TCC AAA GAT ACA ATG GAA GTG AGT AGC AGT GTT GAA TAGCTTTCC AGGACAA           1402
Ser Lys Asp Thr Met Glu Val Ser Ser Ser Val Glu
            445                 450

CCTGAATTCT ATAAGTTCTT GTTTTCTGTT TCCTATGTTT TCTTAAAAAA TAGCATTGAG            1462
ACTTGTGTAG ATGCTTCTCA GAACATGAAA TCAAATTGGA AATCTGTAAC GCAGCTTCTG            1522
TAAGCATGTG TGGGCAAAAA AGCAATAATC CTACTCCTCA AAATAGAAAG TTGAAGATTG            1582
CTGAAAAATA TGACTTTTCT GTATGTTAGA GAAAAACTTT ATGAGGATGA AATGGGTTCA            1642
AGATGAATTT GTCAACTTTT GTCTTCCATT GTTCAGTATT TTAATTATC ACTGTAAATA             1702
ACATTACCAC AAGGCAAAAA AAAAAGAAAA                                             1732
```

( 2 ) INFORMATION FOR SEQ ID NO:18:

( i ) SEQUENCE CHARACTERISTICS:
  ( A ) LENGTH: 453 amino acids
  ( B ) TYPE: amino acid
  ( C ) STRANDEDNESS: single
  ( D ) TOPOLOGY: linear ( i i ) MOLECULE TYPE: protein ( v ) FRAGMENT TYPE: internal ( x i ) SEQUENCE DESCRIPTION: SEQ ID NO:18:

```
Met  Ala  Ser  Ser  Leu  Pro  Trp  Leu  Cys  Ile  Ile  Leu  Trp  Leu  Glu  Asn
 1              5                        10                       15

Ala  Leu  Gly  Lys  Leu  Glu  Val  Glu  Gly  Asn  Phe  Tyr  Ser  Glu  Asn  Val
               20                        25                       30

Ser  Arg  Ile  Leu  Asp  Asn  Leu  Leu  Glu  Gly  Tyr  Asp  Asn  Arg  Leu  Arg
          35                        40                       45

Pro  Gly  Phe  Gly  Gly  Ala  Val  Thr  Glu  Val  Lys  Thr  Asp  Ile  Tyr  Val
     50                        55                       60

Thr  Ser  Phe  Gly  Pro  Val  Ser  Asp  Val  Glu  Met  Glu  Tyr  Thr  Met  Asp
65                       70                       75                       80

Val  Phe  Phe  Arg  Gln  Thr  Trp  Thr  Asp  Glu  Arg  Leu  Lys  Phe  Gly  Gly
                    85                       90                       95

Pro  Thr  Glu  Ile  Leu  Ser  Leu  Asn  Asn  Leu  Met  Val  Ser  Lys  Ile  Trp
               100                      105                      110

Thr  Pro  Asp  Thr  Phe  Phe  Arg  Asn  Gly  Lys  Lys  Ser  Ile  Ala  His  Asn
          115                      120                      125

Met  Thr  Thr  Pro  Asn  Lys  Leu  Phe  Arg  Ile  Met  Gln  Asn  Gly  Thr  Ile
     130                      135                      140

Leu  Tyr  Thr  Met  Arg  Leu  Thr  Ile  Asn  Ala  Asp  Cys  Pro  Met  Arg  Leu
145                      150                      155                      160

Val  Asn  Phe  Pro  Met  Asp  Gly  His  Ala  Cys  Pro  Leu  Lys  Phe  Gly  Ser
                    165                      170                      175

Tyr  Ala  Tyr  Pro  Lys  Ser  Glu  Ile  Ile  Tyr  Thr  Trp  Lys  Lys  Gly  Pro
               180                      185                      190

Leu  Tyr  Ser  Val  Glu  Val  Pro  Glu  Glu  Ser  Ser  Ser  Leu  Leu  Gln  Tyr
          195                      200                      205

Asp  Leu  Ile  Gly  Gln  Thr  Val  Ser  Ser  Glu  Thr  Ile  Lys  Ser  Asn  Thr
     210                      215                      220

Gly  Glu  Tyr  Val  Ile  Met  Thr  Val  Tyr  Phe  His  Leu  Gln  Arg  Lys  Met
225                      230                      235                      240

Gly  Tyr  Phe  Met  Ile  Gln  Ile  Tyr  Thr  Pro  Cys  Ile  Met  Thr  Val  Ile
                    245                      250                      255

Leu  Ser  Gln  Val  Ser  Phe  Trp  Ile  Asn  Lys  Glu  Ser  Val  Pro  Ala  Arg
               260                      265                      270

Thr  Val  Leu  Gly  Ile  Thr  Thr  Val  Leu  Thr  Met  Thr  Thr  Leu  Ser  Ile
          275                      280                      285

Ser  Ala  Arg  His  Ser  Leu  Pro  Lys  Val  Ser  Tyr  Ala  Thr  Ala  Met  Asp
     290                      295                      300

Trp  Phe  Ile  Ala  Val  Cys  Phe  Ala  Phe  Val  Phe  Ser  Ala  Leu  Ile  Glu
305                      310                      315                      320

Phe  Ala  Ala  Val  Asn  Tyr  Phe  Thr  Asn  Leu  Gln  Thr  Gln  Lys  Ala  Lys
                    325                      330                      335

Arg  Lys  Ala  Gln  Phe  Ala  Ala  Pro  Pro  Thr  Val  Thr  Ile  Ser  Lys  Ala
               340                      345                      350

Thr  Glu  Pro  Leu  Glu  Ala  Glu  Ile  Val  Leu  His  Pro  Asp  Ser  Lys  Tyr
```

|   |   |   | 355 |   |   |   |   | 360 |   |   |   |   | 365 |   |   |
|---|---|---|---|---|---|---|---|---|---|---|---|---|---|---|---|
| His | Leu | Lys | Lys | Arg | Ile | Thr | Ser | Leu | Ser | Leu | Pro | Ile | Val | Ser | Ser |
|   | 370 |   |   |   |   | 375 |   |   |   |   | 380 |   |   |   |   |
| Ser | Glu | Ala | Asn | Lys | Val | Leu | Thr | Arg | Ala | Pro | Ile | Leu | Gln | Ser | Thr |
| 385 |   |   |   | 390 |   |   |   |   | 395 |   |   |   |   |   | 400 |
| Pro | Val | Thr | Pro | Pro | Pro | Leu | Pro | Pro | Ala | Phe | Gly | Gly | Thr | Ser | Lys |
|   |   |   |   | 405 |   |   |   |   | 410 |   |   |   |   | 415 |   |
| Ile | Asp | Gln | Tyr | Ser | Arg | Ile | Leu | Phe | Pro | Val | Ala | Phe | Ala | Gly | Phe |
|   |   |   | 420 |   |   |   |   | 425 |   |   |   |   | 430 |   |   |
| Asn | Leu | Val | Tyr | Trp | Val | Val | Tyr | Leu | Ser | Lys | Asp | Thr | Met | Glu | Val |
|   |   | 435 |   |   |   |   | 440 |   |   |   |   | 445 |   |   |   |
| Ser | Ser | Ser | Val | Glu |   |   |   |   |   |   |   |   |   |   |   |
|   |   | 450 |   |   |   |   |   |   |   |   |   |   |   |   |   |

( 2 ) INFORMATION FOR SEQ ID NO:19:

( i ) SEQUENCE CHARACTERISTICS:
        ( A ) LENGTH: 1866 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Coding Sequence
        ( B ) LOCATION: 225...1646
        ( D ) OTHER INFORMATION:

( x i ) SEQUENCE DESCRIPTION: SEQ ID NO:19:

| GAATTCCGCG | CGGGGAAGGG | AAGAAGAGGA | CGAGGTGGCG | CAGAGACCGC | GGGAGAACAC | 60 |
|---|---|---|---|---|---|---|
| AGTGCCTCCG | GAGGAAATCT | GCTCGGTCCC | CGGCAGCCGC | GCTTCCCCTT | TGATGTTTTG | 120 |
| GTACGCCGTG | GCCATGCGCC | TCACATTAGA | ATTACTGCAC | TGGGCAGACT | AAGTTGGATC | 180 |
| TCCTCTCTTC | AGTGAAACCC | TCAATTCCAT | CAAAAACTAA | AGGG ATG TGG AGA GTG | | 236 |
|   |   |   |   | Met Trp Arg Val | | |
|   |   |   |   | 1 | | |

|   |   |   |   |   |   |   |   |   |   |   |   |   |   |   |   |
|---|---|---|---|---|---|---|---|---|---|---|---|---|---|---|---|
| CGG | AAA | AGG | GGC | TAC | TTT | GGG | ATT | TGG | TCC | TTC | CCC | TTA | ATA | ATC | GCC | 284 |
| Arg | Lys | Arg | Gly | Tyr | Phe | Gly | Ile | Trp | Ser | Phe | Pro | Leu | Ile | Ile | Ala |   |
| 5 |   |   |   |   | 10 |   |   |   |   | 15 |   |   |   |   | 20 |   |
| GCT | GTC | TGT | GCG | CAG | AGT | GTC | AAT | GAC | CCT | AGT | AAT | ATG | TCG | CTG | GTT | 332 |
| Ala | Val | Cys | Ala | Gln | Ser | Val | Asn | Asp | Pro | Ser | Asn | Met | Ser | Leu | Val |   |
|   |   |   |   | 25 |   |   |   |   | 30 |   |   |   |   | 35 |   |   |
| AAA | GAG | ACG | GTG | GAT | AGA | CTC | CTG | AAA | GGC | TAT | GAC | ATT | CGT | CTG | AGA | 380 |
| Lys | Glu | Thr | Val | Asp | Arg | Leu | Leu | Lys | Gly | Tyr | Asp | Ile | Arg | Leu | Arg |   |
|   |   |   | 40 |   |   |   |   | 45 |   |   |   |   | 50 |   |   |   |
| CCA | GAT | TTT | GGA | GGT | CCC | CCC | GTG | GCT | GTG | GGG | ATG | AAC | ATT | GAC | ATT | 428 |
| Pro | Asp | Phe | Gly | Gly | Pro | Pro | Val | Ala | Val | Gly | Met | Asn | Ile | Asp | Ile |   |
|   |   | 55 |   |   |   |   | 60 |   |   |   |   | 65 |   |   |   |   |
| GCC | AGC | ATC | GAT | ATG | GTT | TCT | GAA | GTC | AAT | ATG | GAT | TAT | ACC | TTG | ACA | 476 |
| Ala | Ser | Ile | Asp | Met | Val | Ser | Glu | Val | Asn | Met | Asp | Tyr | Thr | Leu | Thr |   |
|   | 70 |   |   |   |   | 75 |   |   |   |   | 80 |   |   |   |   |   |
| ATG | TAC | TTT | CAA | CAA | GCC | TGG | AGA | GAT | AAG | AGG | CTG | TCC | TAT | AAT | GTA | 524 |
| Met | Tyr | Phe | Gln | Gln | Ala | Trp | Arg | Asp | Lys | Arg | Leu | Ser | Tyr | Asn | Val |   |
| 85 |   |   |   |   | 90 |   |   |   |   | 95 |   |   |   |   | 100 |   |
| ATA | CCT | TTA | AAC | TTG | ACT | CTG | GAC | AAC | AGA | GTG | GCA | GAC | CAG | CTC | TGG | 572 |
| Ile | Pro | Leu | Asn | Leu | Thr | Leu | Asp | Asn | Arg | Val | Ala | Asp | Gln | Leu | Trp |   |
|   |   |   |   | 105 |   |   |   |   | 110 |   |   |   |   | 115 |   |   |
| GTG | CCT | GAT | ACC | TAT | TTC | CTG | AAC | GAT | AAG | AAG | TCA | TTT | GTG | CAC | GGA | 620 |
| Val | Pro | Asp | Thr | Tyr | Phe | Leu | Asn | Asp | Lys | Lys | Ser | Phe | Val | His | Gly |   |
|   |   |   | 120 |   |   |   |   | 125 |   |   |   |   | 130 |   |   |   |

| | | | | | | | | | | | | | | | |
|---|---|---|---|---|---|---|---|---|---|---|---|---|---|---|---|
| GTG | ACT | GTT | AAG | AAC | CGC | ATG | ATT | CGC | CTG | CAT | CCT | GAT | GGC | ACC | GTC |
| Val | Thr | Val 135 | Lys | Asn | Arg | Met 140 | Ile | Arg | Leu | His | Pro | Asp 145 | Gly | Thr | Val |

668

| | | | | | | | | | | | | | | | |
|---|---|---|---|---|---|---|---|---|---|---|---|---|---|---|---|
| CTT | TAT | GGA | CTC | AGA | ATC | ACA | ACC | ACA | GCT | GCC | TGC | ATG | ATG | GAC | CTA |
| Leu | Tyr 150 | Gly | Leu | Arg | Ile | Thr 155 | Thr | Thr | Ala | Ala | Cys 160 | Met | Met | Asp | Leu |

716

| | | | | | | | | | | | | | | | |
|---|---|---|---|---|---|---|---|---|---|---|---|---|---|---|---|
| AGG | AGG | TAC | CCA | CTG | GAT | GAA | CAA | AAC | TGC | ACC | TTG | GAA | ATT | GAG | AGC |
| Arg 165 | Arg | Tyr | Pro | Leu | Asp 170 | Glu | Gln | Asn | Cys | Thr 175 | Leu | Glu | Ile | Glu | Ser 180 |

764

| | | | | | | | | | | | | | | | |
|---|---|---|---|---|---|---|---|---|---|---|---|---|---|---|---|
| TAT | GGA | TAC | ACA | ACT | GAT | GAC | ATT | GAG | TTT | TAC | TGG | CGT | GGC | GAT | GAT |
| Tyr | Gly | Tyr | Thr | Thr 185 | Asp | Asp | Ile | Glu | Phe 190 | Tyr | Trp | Arg | Gly | Asp 195 | Asp |

812

| | | | | | | | | | | | | | | | |
|---|---|---|---|---|---|---|---|---|---|---|---|---|---|---|---|
| AAT | GCA | GTA | ACA | GGA | GTA | ACG | AAA | ATT | GAA | CTT | CCA | CAG | TTC | TCT | ATT |
| Asn | Ala | Val | Thr 200 | Gly | Val | Thr | Lys | Ile 205 | Glu | Leu | Pro | Gln | Phe 210 | Ser | Ile |

860

| | | | | | | | | | | | | | | | |
|---|---|---|---|---|---|---|---|---|---|---|---|---|---|---|---|
| GTA | GAT | TAC | AAA | CTT | ATC | ACC | AAG | AAG | GTT | GTT | TTT | TCC | ACA | GGT | TCC |
| Val | Asp | Tyr 215 | Lys | Leu | Ile | Thr 220 | Lys | Lys | Val | Val | Phe 225 | Ser | Thr | Gly | Ser |

908

| | | | | | | | | | | | | | | | |
|---|---|---|---|---|---|---|---|---|---|---|---|---|---|---|---|
| TAT | CCC | AGG | TTA | TCC | CTC | AGC | TTT | AAG | CTT | AAG | AGA | AAC | ATT | GGC | TAC |
| Tyr | Pro | Arg 230 | Leu | Ser | Leu | Ser 235 | Phe | Lys | Leu | Lys | Arg 240 | Asn | Ile | Gly | Tyr |

956

| | | | | | | | | | | | | | | | |
|---|---|---|---|---|---|---|---|---|---|---|---|---|---|---|---|
| TTT | ATC | CTG | CAA | ACA | TAC | ATG | CCT | TCC | ATC | CTG | ATT | ACC | ATC | CTC | TCC |
| Phe 245 | Ile | Leu | Gln | Thr | Tyr 250 | Met | Pro | Ser | Ile | Leu 255 | Ile | Thr | Ile | Leu | Ser 260 |

1004

| | | | | | | | | | | | | | | | |
|---|---|---|---|---|---|---|---|---|---|---|---|---|---|---|---|
| TGG | GTC | TCC | TTC | TGG | ATT | AAT | TAC | GAT | GCT | TCA | GCT | GCA | AGG | GTG | GCA |
| Trp | Val | Ser | Phe | Trp 265 | Ile | Asn | Tyr | Asp | Ala 270 | Ser | Ala | Ala | Arg | Val 275 | Ala |

1052

| | | | | | | | | | | | | | | | |
|---|---|---|---|---|---|---|---|---|---|---|---|---|---|---|---|
| TTA | GGA | ATC | ACA | ACT | GTC | CTC | ACA | ATG | ACC | ACA | ATC | AAC | ACC | CAC | CTC |
| Leu | Gly | Ile | Thr 280 | Thr | Val | Leu | Thr | Met 285 | Thr | Thr | Ile | Asn | Thr 290 | His | Leu |

1100

| | | | | | | | | | | | | | | | |
|---|---|---|---|---|---|---|---|---|---|---|---|---|---|---|---|
| CGG | GAA | ACT | CTC | CCT | AAA | ATC | CCC | TAT | GTG | AAG | GCC | ATT | GAC | ATG | TAC |
| Arg | Glu | Thr 295 | Leu | Pro | Lys | Ile | Pro 300 | Tyr | Val | Lys | Ala | Ile 305 | Asp | Met | Tyr |

1148

| | | | | | | | | | | | | | | | |
|---|---|---|---|---|---|---|---|---|---|---|---|---|---|---|---|
| CTG | ATG | GGG | TGC | TTT | GTC | TTC | GTT | TTC | ATG | GCC | CTT | CTG | GAA | TAT | GCC |
| Leu | Met 310 | Gly | Cys | Phe | Val | Phe 315 | Val | Phe | Met | Ala | Leu 320 | Leu | Glu | Tyr | Ala |

1196

| | | | | | | | | | | | | | | | |
|---|---|---|---|---|---|---|---|---|---|---|---|---|---|---|---|
| CTA | GTC | AAC | TAC | ATC | TTC | TTT | GGG | AGG | GGG | CCC | CAA | CGC | CAA | AAG | AAA |
| Leu 325 | Val | Asn | Tyr | Ile | Phe 330 | Phe | Gly | Arg | Gly | Pro 335 | Gln | Arg | Gln | Lys | Lys 340 |

1244

| | | | | | | | | | | | | | | | |
|---|---|---|---|---|---|---|---|---|---|---|---|---|---|---|---|
| GCA | GCT | GAG | AAG | GCT | GCC | AGT | GCC | AAC | AAT | GAG | AAG | ATG | CGC | CTG | GAT |
| Ala | Ala | Glu | Lys | Ala 345 | Ala | Ser | Ala | Asn | Asn 350 | Glu | Lys | Met | Arg | Leu 355 | Asp |

1292

| | | | | | | | | | | | | | | | |
|---|---|---|---|---|---|---|---|---|---|---|---|---|---|---|---|
| GTC | AAC | AAG | ATG | GAC | CCC | CAT | GAG | AAC | ATC | TTA | CTG | AGC | ACT | CTC | GAG |
| Val | Asn | Lys | Met 360 | Asp | Pro | His | Glu | Asn 365 | Ile | Leu | Leu | Ser | Thr 370 | Leu | Glu |

1340

| | | | | | | | | | | | | | | | |
|---|---|---|---|---|---|---|---|---|---|---|---|---|---|---|---|
| ATA | AAA | AAT | GAA | ATG | GCC | ACA | TCT | GAG | GCT | GTG | ATG | GGA | CTT | GGA | GAC |
| Ile | Lys | Asn 375 | Glu | Met | Ala | Thr | Ser 380 | Glu | Ala | Val | Met | Gly 385 | Leu | Gly | Asp |

1388

| | | | | | | | | | | | | | | | |
|---|---|---|---|---|---|---|---|---|---|---|---|---|---|---|---|
| CCC | AGA | AGC | ACA | ATG | CTA | GCC | TAT | GAT | GCC | TCC | AGC | ATC | CAG | TAT | CGG |
| Pro | Arg | Ser | Thr 390 | Met | Leu | Ala | Tyr | Asp 395 | Ala | Ser | Ser | Ile | Gln 400 | Tyr | Arg |

1436

| | | | | | | | | | | | | | | | |
|---|---|---|---|---|---|---|---|---|---|---|---|---|---|---|---|
| AAA | GCT | GGG | TTG | CCC | AGG | CAT | AGT | TTT | GGC | CGA | AAT | GCT | CTG | GAA | CGA |
| Lys 405 | Ala | Gly | Leu | Pro | Arg 410 | His | Ser | Phe | Gly | Arg 415 | Asn | Ala | Leu | Glu | Arg 420 |

1484

| | | | | | | | | | | | | | | | |
|---|---|---|---|---|---|---|---|---|---|---|---|---|---|---|---|
| CAT | GTG | GCG | CAA | AAG | AAA | AGT | CGC | CTG | AGG | AGA | CGC | GCC | TCC | CAA | CTG |
| His | Val | Ala | Gln | Lys 425 | Lys | Ser | Arg | Leu | Arg 430 | Arg | Arg | Ala | Ser | Gln 435 | Leu |

1532

| | | | | | | | | | | | | | | | |
|---|---|---|---|---|---|---|---|---|---|---|---|---|---|---|---|
| AAA | ATC | ACC | ATC | CCT | GAC | TTG | ACT | GAT | GTG | AAT | GCC | ATA | GAT | CGG | TGG |
| Lys | Ile | Thr | Ile 440 | Pro | Asp | Leu | Thr | Asp 445 | Val | Asn | Ala | Ile | Asp 450 | Arg | Trp |

1580

```
TCC CGC ATA TTC TTC CCA GTG GTT TTT TCC TTC TTC AAC ATC GTC TAT       1628
Ser Arg Ile Phe Phe Pro Val Val Phe Ser Phe Phe Asn Ile Val Tyr
        455             460                 465

TGG CTT TAT TAT GTG AAC TAAAACATGG CCTCCCACTG GAAGCAAGGA CTAGATTCC    1685
Trp Leu Tyr Tyr Val Asn
        470

TCCTCAAACC AGTTGTACAG CCTGATGTAG GACTTGGAAA ACACATCAAT CCAGGACAAA     1745

AGTGACGCTA AAATACCTTA GTTGCTGGCC TATCCTGTGG TCCATTTCAT ACCATTTGGG     1805

TTGCTTCTGC TAAGTAATGA ATACACTAAG GTCCTTGTGG TTTTCCAGTT AAAACGCAAG     1865

T                                                                    1866
```

( 2 ) INFORMATION FOR SEQ ID NO:20:

( i ) SEQUENCE CHARACTERISTICS:
        ( A ) LENGTH: 474 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:20:

```
Met Trp Arg Val Arg Lys Arg Gly Tyr Phe Gly Ile Trp Ser Phe Pro
 1               5                  10                  15

Leu Ile Ile Ala Ala Val Cys Ala Gln Ser Val Asn Asp Pro Ser Asn
                20                  25                  30

Met Ser Leu Val Lys Glu Thr Val Asp Arg Leu Leu Lys Gly Tyr Asp
            35                  40                  45

Ile Arg Leu Arg Pro Asp Phe Gly Gly Pro Pro Val Ala Val Gly Met
        50                  55                  60

Asn Ile Asp Ile Ala Ser Ile Asp Met Val Ser Glu Val Asn Met Asp
 65                  70                  75                  80

Tyr Thr Leu Thr Met Tyr Phe Gln Gln Ala Trp Arg Asp Lys Arg Leu
                85                  90                  95

Ser Tyr Asn Val Ile Pro Leu Asn Leu Thr Leu Asp Asn Arg Val Ala
                100                 105                 110

Asp Gln Leu Trp Val Pro Asp Thr Tyr Phe Leu Asn Asp Lys Lys Ser
            115                 120                 125

Phe Val His Gly Val Thr Val Lys Asn Arg Met Ile Arg Leu His Pro
        130                 135                 140

Asp Gly Thr Val Leu Tyr Gly Leu Arg Ile Thr Thr Thr Ala Ala Cys
145                 150                 155                 160

Met Met Asp Leu Arg Arg Tyr Pro Leu Asp Glu Gln Asn Cys Thr Leu
                165                 170                 175

Glu Ile Glu Ser Tyr Gly Tyr Thr Thr Asp Asp Ile Glu Phe Tyr Trp
            180                 185                 190

Arg Gly Asp Asp Asn Ala Val Thr Gly Val Thr Lys Ile Glu Leu Pro
        195                 200                 205

Gln Phe Ser Ile Val Asp Tyr Lys Leu Ile Thr Lys Lys Val Val Phe
    210                 215                 220

Ser Thr Gly Ser Tyr Pro Arg Leu Ser Leu Ser Phe Lys Leu Lys Arg
225                 230                 235                 240

Asn Ile Gly Tyr Phe Ile Leu Gln Thr Tyr Met Pro Ser Ile Leu Ile
                245                 250                 255

Thr Ile Leu Ser Trp Val Ser Phe Trp Ile Asn Tyr Asp Ala Ser Ala
```

-continued

```
                    260                         265                         270
Ala Arg Val Ala Leu Gly Ile Thr Thr Val Leu Thr Met Thr Thr Ile
        275                 280                 285

Asn Thr His Leu Arg Glu Thr Leu Pro Lys Ile Pro Tyr Val Lys Ala
    290                 295                 300

Ile Asp Met Tyr Leu Met Gly Cys Phe Val Phe Val Phe Met Ala Leu
305                 310                 315                     320

Leu Glu Tyr Ala Leu Val Asn Tyr Ile Phe Phe Gly Arg Gly Pro Gln
                325                 330                     335

Arg Gln Lys Lys Ala Ala Glu Lys Ala Ala Ser Ala Asn Asn Glu Lys
            340                 345                 350

Met Arg Leu Asp Val Asn Lys Met Asp Pro His Glu Asn Ile Leu Leu
        355                 360                 365

Ser Thr Leu Glu Ile Lys Asn Glu Met Ala Thr Ser Glu Ala Val Met
    370                 375                 380

Gly Leu Gly Asp Pro Arg Ser Thr Met Leu Ala Tyr Asp Ala Ser Ser
385                 390                 395                     400

Ile Gln Tyr Arg Lys Ala Gly Leu Pro Arg His Ser Phe Gly Arg Asn
            405                 410                 415

Ala Leu Glu Arg His Val Ala Gln Lys Lys Ser Arg Leu Arg Arg Arg
            420                 425                 430

Ala Ser Gln Leu Lys Ile Thr Ile Pro Asp Leu Thr Asp Val Asn Ala
        435                 440                 445

Ile Asp Arg Trp Ser Arg Ile Phe Phe Pro Val Val Phe Ser Phe Phe
    450                 455                 460

Asn Ile Val Tyr Trp Leu Tyr Tyr Val Asn
465                 470
```